(12) United States Patent
Meller et al.

(10) Patent No.: US 11,796,531 B2
(45) Date of Patent: Oct. 24, 2023

(54) LIGHT-ENHANCING PLASMONIC NANOWELL-NANOPORE BIOSENSOR AND USE THEREOF

(71) Applicant: TECHNION RESEARCH & DEVELOPMENT FOUNDATION LIMITED, Haifa (IL)

(72) Inventors: Amit Meller, Haifa (IL); Ossama Assad, Nazareth (IL); Tal Gilboa, Haifa (IL); Joshua Spitzberg, Tel Aviv (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 417 days.

(21) Appl. No.: 16/955,307

(22) PCT Filed: Dec. 20, 2018

(86) PCT No.: PCT/IL2018/051383
§ 371 (c)(1),
(2) Date: Jun. 18, 2020

(87) PCT Pub. No.: WO2019/123467
PCT Pub. Date: Jun. 27, 2019

(65) Prior Publication Data
US 2021/0003547 A1   Jan. 7, 2021

Related U.S. Application Data

(60) Provisional application No. 62/608,013, filed on Dec. 20, 2017.

(51) Int. Cl.
*G01N 33/487* (2006.01)
*C12Q 1/68* (2018.01)
(Continued)

(52) U.S. Cl.
CPC ..... *G01N 33/48721* (2013.01); *C12Q 1/6869* (2013.01); *G01N 21/6428* (2013.01); *G01N 2021/6439* (2013.01)

(58) Field of Classification Search
CPC .......... C12Q 1/6869; G01N 33/48721; G01N 21/6428; G01N 2021/6439
See application file for complete search history.

(56) References Cited

U.S. PATENT DOCUMENTS

2013/0203050 A1\* 8/2013 Huber .................. C12Q 1/6876
435/287.2
2018/0266980 A1\* 9/2018 Cicero ............... G01N 27/3277

OTHER PUBLICATIONS

Assad et al. "Light-Enhancing Plasmonic-Nanopore Biosensor for Superior Single-Molecule Detection". Advanced Materials, 29, 1605442 pp. 2-9 (Mar. 7, 2017; ePub 2016) with Supporting Information. (Year: 2017).\*

(Continued)

*Primary Examiner* — Jezia Riley
(74) *Attorney, Agent, or Firm* — The Roy Gross Law Firm, LLC; Roy Gross

(57) ABSTRACT

Systems for detecting fluorescence from a molecule comprising an ion-impermeable film comprising at least one ion-conducting nanopore; a first and second liquid reservoir separated by the film; a means to induce movement of the molecule from the first reservoir to the second reservoir via the nanopore; a light source capable of exciting the molecule to emit fluorescence, wherein the light source shines into the second reservoir; a metallic layer adhered to the film by an adhesion layer and comprising a nanowell structure located adjacent to the nanopore; and a detector configured to detect the fluorescence emitted by the molecule are provided. Methods of use of the systems are also provided.

20 Claims, 27 Drawing Sheets
(24 of 27 Drawing Sheet(s) Filed in Color)

(51) Int. Cl.
*C12Q 1/6869* (2018.01)
*G01N 21/64* (2006.01)

(56) References Cited

OTHER PUBLICATIONS

Assad, O. N., Gilboa, T., Spitzberg, J., Juhasz, M., Weinhold, E., & Meller, A. (2017). Light-enhancing plasmonic-nanopore biosensor for superior single-molecule detection. Advanced Materials, 29(9), 1605442. epub 2016. DOI: 10.1002/adma.201605442.
Branton D, et al. The potential and challenges of nanopore sequencing. Nat Biotechnol. Oct. 2008;26(10):1146-53. doi: 10.1038/nbt. 1495. PMID: 18846088; PMCID: PMC2683588; doi:10.1038/nbt. 1495.
Kasianowicz JJ, Brandin E, Branton D, Deamer DW. Characterization of individual polynucleotide molecules using a membrane channel. Proc Natl Acad Sci USA. Nov. 26, 1996;93(24):13770-3. doi:10.1073/pnas.93.24.13770. PMID: 8943010; PMCID: PMC19421.
Weller, A. (2012). Nanopores: Single-Molecule Sensors of Nucleic Acid-Based Complexes. In S. A. Rice & A. R. Dinnen (Eds.), Advances in Chemical Physics (vol. 149, p. 251). John Wiley & Sons, Inc. https://doiorg/10.1002/9781118180396.ch6.
Meller, A., Nivón, L., Brandin, E. Golovchenko, J. & Branton, D. (2000). Rapid Nanopore Discrimination Between Single Polynucleotide Molecules. Proceedings of the National Academy of Sciences of the United States of America. 97. 1079-84. doi: 10.1073/pnas.97.3. 1079.
Venkatesan, B. M., & Bashir, R. (2011). Nanopore sensors for nucleic acid analysis. Nature Nanotechnology, 6(10), 615-624. doi:10.1038/nnano.2011.129.
Firnkes, M. et al., Electrically Facilitated Translocations of Proteins through Silicon Nitride Nanopores: Conjoint and Competitive Action of Diffusion, Electrophoresis, and Electroosmosis. Nano Letters 2010 10 (6), 2162-2167 DOI: 10.1021/nl100861c.
Larkin J, Henley RY, Muthukumar M, Rosenstein JK, Wanunu M. High-bandwidth protein analysis using solid-state nanopores. Biophys J. Feb. 4, 2014;106(3):696-704. doi: 10.1016/j.bpj.2013.12.025. PMID: 24507610; PMCID: PMC3944622.
Yusko, E.C., Johnson, J.M., Majd, S., Prangkio, P., Rollings, R.C., Li, J., Yang, J. & Mayer, M. Controlling protein translocation through nanopores with bio-inspired fluid walls. Nat Nanotechnol. Apr. 2011;6(4):253-60. doi: 10.1038/nnano.2011.12. Epub Feb. 20, 2011. PMID: 21336266; PMCID: PMC3071889.
Wu, H. C., & Bayley, H. (2008). Single-molecule detection of nitrogen mustards by covalent reaction within a protein nanopore. Journal of the American Chemical Society, 130(21), 6813-6819.
Deamer, D., Akeson, M., & Branton, D. (2016). Three decades of nanopore sequencing. Nature biotechnology, 34(5), 518-524.
Ayub, M., Hardwick, S.W., Luisi, B.F. & Bayley, H. Nanopore-based identification of individual nucleotides for direct RNA sequencing. Nano Lett. 2013;13(12):6144-50. doi: 10.1021/nl403469r. Epub Nov. 13, 2013. PMID: 24171554; PMCID: PMC3899427.
Cherf, G.M., Lieberman, K.R., Rashid, H., Lam, C.E., Karplus, K. & Akeson, M. Automated forward and reverse ratcheting of DNA in a nanopore at 5-Å precision. Nat Biotechnol. Feb. 14, 2012;30(4):344-8. doi: 10.1038/nbt.2147. PMID: 22334048; PMCID: PMC3408072.
Feng, J., Liu, K., Bulushev, R.D., Khlybov, S., Dumcenco, D., Kis, A. & Radenovic, A. Identification of single nucleotides in MoS2 nanopores. Nat Nanotechnol. Dec. 2015;10(12):1070-6. doi: 10.1038/ nnano.2015.219. Epub Sep. 21, 2015. PMID: 26389660.
Cao, C., Ying, Y.L., Hu, Z.L., Liao, D.F., Tian, H. & Long, Y.T. Discrimination of oligonucleotides of different lengths with a wild-type aerolysin nanopore. Nat Nanotechnol. Aug. 2016;11(8):713-8. doi: 10.1038/nnano.2016.66. Epub Apr. 25, 2016 PMID: 27111839.
Laszlo, A.H., Derrington, I.M., Ross, B.C., Brinkerhoff, H., Adey, A., Nova, I.C., Craig, J.M., Langford, K.W., Samson, J.M., Daza, R., Doering, K., Shendure, J. & Gundlach, J.H. Decoding long nanopore sequencing reads of natural DNA. Nat Biotechnol. Aug. 2014;32(8):829-33. doi: 10.1038/nbt.2950. Epub Jun. 25, 2014. PMID: 24964173; PMCID: PMC4126851.
Manrao, E.A., Derrington, I.M., Laszlo, A.H., Langford, K.W., Hopper, M.K., Gillgren, N., Pavlenok, M., Niederweis, M., & Gundlach, J.H. Reading DNA at single-nucleotide resolution with a mutant MspA nanopore and phi29 DNA polymerase. Nat Biotechnol. Mar. 25, 2012;30(4):349-53. doi: 10.1038/nbt.2171. PMID: 22446694; PMCID: PMC3757088.
Wanunu, M.. Nanopores: A journey towards DNA sequencing. Phys Life Rev. Jun. 2012;9(2):125-58. doi: 10.1016/j.plrev.2012.05.010. Epub May 18, 2012. PMID: 22658507; PMCID: PMC3780799.
Traversi,F., Raillon, C., Benameur, S.M., Liu, K., Khlybov, S., Tosun, M., Krasnozhon, D., Kis, A. & Radenovic, A. Detecting the translocation of DNA through a nanopore using graphene nanoribbons. Nat Nanotechnol. Dec. 2013;8(12):939-45. doi: 10.1038/ nnano.2013.240. Epub Nov. 17, 2013. PMID: 24240429.
Tsutsui, M., Taniguchi, M., Yokota, K., & Kawai, T. (2010). Identifying single nucleotides by tunnelling current. Nature nanotechnology, 5(4), 286-290. Nature Nanotechnology, 5 (4): 286-90. DOI:10.1038/nnano.2010.42.
McNally, B., Singer, A., Yu, Z., Sun, Y., Weng, Z., & Meller, A. Optical recognition of converted DNA nucleotides for single-molecule DNA sequencing using nanopore arrays. Nano Lett. Jun. 9, 2010;10(6):2237-44. doi: 10.1021/nl1012147. PMID: 20459065; PMCID: PMC2883017.
Gilboa, T., & Meller, A. (2015). Optical sensing and analyte manipulation in solid-state nanopores. Analyst, 140(14), 4733-4747. DOI:10.1039/c4an02388a.
Brett N. Anderson et al. Probing Solid-State Nanopores with Light for the Detection of Unlabeled Analytes. ACS Nano 2014 8(11), 11836-11845 DOI: 10.1021/nn505545h.
Ivankin, A., Henley, R.Y., Larkin, J., Carson, S., Toscano, M.L.& Wanunu, M. Label-free optical detection of biomolecular translocation through nanopore arrays. ACS Nano. Oct. 28, 2014;8(10):10774-81. doi: 10.1021/nn504551d. Epub Sep. 22, 2014. PMID: 25232895; PMCID: PMC4212781.
Ossama N. Assad, Nicolas Di Fiori, Allison H. Squires, and Amit Meller. Two Color DNA Barcode Detection in Photoluminescence Suppressed Silicon Nitride Nanopores. Nano Letters 2015 15 (1), 745-752 DOI: 10.1021/nl504459c.
Yamazaki, H., Kimura, S., Tsukahara, M., Esashika, K., & Saiki, T. (2014). Optical detection of DNA translocation through silicon nanopore by ultraviolet light. Applied Physics A: Materials Science and Processing, 115(1), 53-56. Epub 2013 https://doi.org/10.1007/ S00339-013-7956-0.
Sawafta, F., Clancy, B., Carlsen, A. T., Huber, M., & Hall, A. R. (2014). Solid-state nanopores and nanopore arrays optimized for optical detection. Nanoscale, 6(12), 6991-6996. doi:10.1039/ c4nr00305e.
Francesca Nicoli, Daniel Verschueren, Misha Klein, Cees Dekker, and Magnus P. Jonsson. DNA Translocations through Solid-State Plasmonic Nanopores. Nano Letters 2014 14 (12), 6917-6925 DOI: 10.1021/nl503034j.
Li, Y., Nicoli, F., Chen, C., Lagae, L., Groeseneken, G., Stakenborg, T., Zandbergen, H.W., Dekker, C., Van Dorpe, P., & Jonsson, M.P.. Photoresistance switching of plasmonic nanopores. Nano Lett. Jan. 14, 2015;15(1):776-82. doi: 10.1021/nl504516d. Epub Dec. 19, 2014. PMID: 25514824; PMCID: PMC4296925.
Crick, C. R., Albella, P., Ng, B., Ivanov, A. P., Roschuk, T., Cecchini, M. P., & Edel, J. B. (2015). Precise attoliter temperature control of nanopore sensors using a nanoplasmonic bullseye. Nano letters, 15(1), 553-559. https://doi.org/10.1021/nl504536j.
Belkin, M., Chao, S. H., Jonsson, M. P., Dekker, C., & Aksimentiev, A. (2015). Plasmonic nanopores for trapping, controlling displacement, and sequencing of DNA. ACS nano, 9(11), 10598-10611. https://doi.org/10.1021/acsnano.5b04173.
S. Kerman, C. Chen, Y. Li, W. Van Roy, L. Lagae, P. Van Dorpe. Raman fingerprinting of single dielectric nanoparticles in plasmonic nanopores. Nanoscale, 2015,7, 18612-18618. DOI:10.1039/ C5NR05341B.
Levene, M.J., Koriach, J., Turner, S.W., Foquet, M., Craighead, H.G. & Webb, W.W.. Zero-mode waveguides for single-molecule

(56) References Cited

OTHER PUBLICATIONS analysis at high concentrations. Science. Jan. 31, 2003;299(5607):682-6. doi: 10.1126/science.1079700. PMID: 12560545.
Eid, J. et al., Real-time DNA sequencing from single polymerase molecules. Science. Jan. 2, 2009;323(5910):133-8. doi: 10.1126/science.1162986. Epub Nov. 20, 2008. PMID: 19023044.
Larkin, J., Foquet, M., Turner, S. W., Koriach, J., & Wanunu, M. (2014). Reversible positioning of single molecules inside zero-mode waveguides. Nano letters, 14(10), 6023-6029. https://doi.org/10.1021/nl503134x.
D. Gérard, J. Wenger, N. Bonod, E. Popov, H. Rigneault, F. Mahdavi, S. Blair, J. Dintinger & T. W. Ebbesen, Nanoaperture-enhanced fluorescence: Towards higher detection rates with plasmonic metals, Phys. Rev. B 2008, 77, 045413. DOI: https://doi.org/10.1103/PhysRevB.77.045413.
M. Foquet, K. T. Samiee, X. Kong, B. P. Chauduri, P. M. Lundquist, S. W. Turner, J. Freudenthal, D. B. & Roitman, J. Improved fabrication of zero-mode waveguides for single-molecule detection. Appl. Phys. 2008, 103, 034301. https://doi.org/10.1063/1.2831366.
Grunwald, A., Dahan, M., Giesbertz, A., Nilsson, A., Nyberg, L.K., Weinhold, E., Ambjörnsson, T., Westerlund, F. & Ebenstein, Y.. Bacteriophage strain typing by rapid single molecule analysis. Nucleic Acids Res. Oct. 15, 2015;43(18): e117. doi: 10.1093/nar/gkv563. Epub May 27, 2015. PMID: 26019180; PMCID: PMC4605287.
Holz, B., Klimasauskas, S., Serva, S. & Weinhold, E. 2-Aminopurine as a fluorescent probe for DNA base flipping by methyltransferases. Nucleic Acids Res. Feb. 15, 1998;26(4):1076-83. doi: 10.1093/nar/26.4.1076. PMID: 9461471; PMCID: PMC147370.
He, Y., Tsutsui, M., Scheicher, R.H., Fan, C., Taniguchi, M. & Kawai, T.. Mechanism of how salt-gradient-induced charges affect the translocation of DNA molecules through a nanopore. Biophys J. Aug. 6, 2013;105(3):776-82. doi: 10.1016/j.bpj.2013.05.065. PMID: 23931325; PMCID: PMC3736693.
Wanunu, M., Morrison, W., Rabin, Y., Grosberg, A.Y. & Meller, A. Electrostatic focusing of unlabelled DNA into nanoscale pores using a salt gradient. Nat Nanotechnol. Feb. 2010;5(2):160-5. doi: 10.1038/nnano.2009.379. Epub Dec. 20, 2009. PMID: 20023645; PMCID: PMC2849735.
A. Kinkhabwala, Z. Yu, S. Fan, Y. Avlasevich, K. Mullen & W. E. Moerner. Large single-molecule fluorescence enhancements produced by a bowtie nanoantenna. Nat. Photon. 2009, 3, 654. Retrieved from: https://doi.org/10.1038/nphoton.2009.187.
Jonsson, M. P., & Dekker, C. (2013). Plasmonic nanopore for electrical profiling of optical intensity landscapes. Nano letters, 13(3), 1029-1033. Retrieved from: https://doi.org/10.1021/nl304213s.
Jérôme Wenger, Davy Gérard, José Dintinger, Oussama Mahboub, Nicolas Bonod, Evgeny Popov, Thomas W. Ebbesen, and Hervé Rigneault, "Emission and excitation contributions to enhanced single molecule fluorescence by gold nanometric apertures," Opt. Express 16, 3008-3020 (2008). doi: 10.1364/oe.16.003008.
PCT International Search Report for International Application No. PCT/IL2018/051383, dated Apr. 3, 2019, 2pp.
PCT Written Opinion for International Application No. PCT/IL2018/051383, dated Apr. 3, 2019, 8pp.
PCT International Preliminary Report on Patentability for International Application No. PCT/IL2018/051383, dated Jun. 23, 2020, 9pp.

\* cited by examiner

LIGHT-ENHANCING PLASMONIC NANOWELL-NANOPORE BIOSENSOR AND USE THEREOF

CROSS REFERENCE TO RELATED APPLICATIONS

This application is a National Phase of PCT Patent Application No. PCT/IL2018/051383 having International filing date of Dec. 20, 2018, which claims the benefit of priority to U.S. Provisional Patent Application No. 62/608,013 filed Dec. 20, 2017, the contents of which are incorporated herein by reference in their entirety.

FIELD OF INVENTION

The present invention is in the field of nanopore biosensors.

BACKGROUND OF THE INVENTION

The development of nanopore-based biosensors has received considerable attention in the past two decades due to their compatibility with a broad range of analytes, including nucleic acids, proteins, and various small molecules. Particularly, nanopore-based DNA sequencing has recently emerged as a viable alternative to sequencing-by-synthesis approaches, offering a highly portable and affordable solution with high throughput and precision. Currently the most advanced nanopore based sequencing methods are based on protein pores, such as the CsgG or MspA channels, which require a ratcheting enzyme to regulate the transport of a DNA strand. Nevertheless, the development of synthetic nanopores remains a major focus in nanotechnology due to the inherent limitations of the protein pores and the greater flexibility that synthetic nanopores offer in term of the ability to tailor their size, shape and surface properties towards specific sensing applications.

Solid-state nanopores (ssNPs) fabricated in thin inorganic membranes can be crafted with sub-nanometer precision to match the size of the target analyte and are therefore considered to be highly attractive platforms. Moreover, ssNPs are compatible with a variety of single-molecule detection methods (in addition to the ion-current resistive-pulse technique) making them ideally suited for the development of future integrated biological sensors. In particular, because ssNPs are fabricated in essentially 2D, solid membranes, they lend themselves to relatively straightforward implementation of optical sensing, which can provide independent and completely orthogonal information on the analytes. As a result, in the past few years electro-optical sensing in ssNPs has gained growing momentum towards applications such as rapid DNA sequencing, DNA barcoding and epi-genetic modification sensing. Notably, ssNPs can be articulated with plasmonic nanostructures to enhance key features of the nanopore sensing. For example, plasmonic structures have been used to produce local heating in the pore vicinity, hence controlling the translocation speed and capture rate of DNA molecules. Moreover, bow-tie structures fabricated around the nanopore were proposed for rapid DNA sequencing utilizing surface-enhanced Raman scattering from nucleotides passing through the pore.

Despite these major advancements in optical sensing in ssNPs, the detection of individual fluorophores has proven to be challenging due to two competing factors: first, when excited by the laser source, solid dielectric membranes (such as SiNx, SiO2, etc.) emit light through photo-luminescence in wavelengths that overlap with the fluorescence emission. This background noise comes on top of the fluorescence background from molecules residing in the detection volume. Second, the dwell time of the fluorophore in the nanopore is relatively short, hence limiting the photon integration time and diminishing the overall signal. A possible solution for these issues involved the incorporation of molecular quenchers for each fluorophore, but this come at the expense of more complex sample preparation. Nanopore biosensors that are quencher-free, produce a stronger signal and with lower background are much in need.

SUMMARY OF THE INVENTION

The present invention provides methods and systems for detecting fluorescence from a molecule.

According to a first aspect, there is provided a system for detecting fluorescence from a molecule, the system comprising:
a. an ion-impermeable film comprising at least one ion-conducting nanopore;
b. a first and a second liquid reservoir separated by the film;
c. a means to induce movement of the molecule from the first reservoir to the second reservoir via the nanopore;
d. a light source capable of exciting the molecule to emit fluorescence, wherein the light source shines into the second reservoir;
e. a metallic layer adhered to the film by an adhesion layer, the metallic layer comprising a nanowell structure located adjacent to the nanopore; and
f. a first detector configured to detect the fluorescence emitted by the molecule.

According to another aspect, there is provided a substrate comprising:
a. an ion impermeable film comprising at least one ion-conducting nonpore; and
b. a metallic layer adhered to said film by an adhesion layer, said metallic layer comprising a nanowell structure located adjacent to said nanopore.

According to some embodiments, the system comprises a substrate of the invention.

According to some embodiments, the metallic layer and the adhesion layer comprise a thickness sufficient to block at least 95% of light emitted by the light source. According to some embodiments, the metallic layer and the adhesion layer comprise a thickness sufficient to block at least 50% of light emitted by the light source.

According to some embodiments, the diameter of the nanowell is not greater than half the wavelength of the light emitted by the light source.

According to some embodiments, the molecule comprises at least one fluorescent moiety. According to some embodiments, the fluorescent moiety is a fluorescent tag. According to some embodiments, the fluorescent moiety is Cy5 or CF640R.

According to some embodiments, the molecule is a nucleic acid molecule or a polypeptide. According to some embodiments, the nucleic acid molecule is any one of single-stranded DNA, double-stranded DNA, RNA, and cDNA. According to some embodiments, the nucleic acid molecule is double-stranded DNA.

According to some embodiments, the film is a silicon-based membrane. According to some embodiments, the membrane is a silicon nitride (SiNx) membrane. According to some embodiments, the film has a thickness of less than 50 nanometers (nm).

According to some embodiments, the nanopore comprises a diameter not greater than 5 nm. According to some embodiments, the film comprises at least 2 nanopores and the nanopores are separated by at least 1 micrometers (μm).

According to some embodiments, the means to induce movement comprises a negative electrode within the first reservoir, and a positive electrode within the second reservoir and the molecule has a negative charge.

According to some embodiments, the light source produces red light. According to some embodiments, the red light source is a laser having wavelength in the range 640 and 650 nm. According to some embodiments, a power of the light source is at most 10 microwatts (μW).

According to some embodiments, the metallic layer comprises a metal selected from gold, silver, copper, aluminum and a combination thereof. According to some embodiments, the metal is gold. According to some embodiments, the metallic layer comprises a thickness of between 100 and 150 nm. According to some embodiments, the metallic layer is on the second reservoir-side of the membrane.

According to some embodiments, the adhesion layer comprises a metal oxide According to some embodiments, the adhesion layer comprises chromium, chromium oxide, titanium or titanium oxide. According to some embodiments, the adhesion layer comprises a thickness of between 1 and 20 nm.

According to some embodiments, the nanopore is at the center of the nanowell. According to some embodiments, the nanowell comprises a diameter between 30 and 150 nm.

According to some embodiments, the detecting comprises sub-millisecond (ms) resolution. According to some embodiments, the detecting comprises a high signal to noise ratio.

According to some embodiments, the first detector is an active pixel sensor (APS). According to some embodiments, the APS is a complementary metal-oxide semiconductor (CMOS) sensor. According to some embodiments, the first detector is a charge coupled device (CCD) detector. According to some embodiments, the first detector is an Avalanche Photo Diode detector.

According to some embodiments, a system of the invention further comprise a second detector configured to detect ion current flow through the nanopore. According to some embodiments, the second detector is configured to convert the ion current through the nanopore to a measurable electrical current. According to some embodiments, the second detector is a high-gain current amplifier. According to some embodiments, the means to induce movement comprises a first electrode within the first reservoir, and a second electrode within the second reservoir, and the high current amplifier is connected to the first and second electrodes. According to some embodiments, the first and the second detector are synchronized.

According to some embodiments, a system of the invention is for use in sequencing the molecule.

According to another aspect, there is provided a method of detecting fluorescence from a single molecule, the method comprising:
 a. introducing the molecule into the first reservoir of a system of the invention;
 b. inducing the molecule to move from the first reservoir to the second reservoir via the nanopore;
 c. exciting the molecule within the nanowell to emit fluorescence; and
 d. detecting the fluorescence emitted by the molecule;
thereby detecting fluorescence from a single molecule.

According to some embodiments, the detecting comprises sub-millisecond (ms) resolution. According to some embodiments, the detecting comprises a high signal to noise ratio.

According to some embodiments, the metallic layer and the adhesion layer block excitation of fluorochromes in the first reservoir and reduce background fluorescence in the system.

According to some embodiments, the nanowell enhances fluorescence from the molecule by at least 5-fold.

According to some embodiments, the system further detects ion current flow through the nanopore and wherein only an event detected simultaneously by fluorescence and electricity is considered detecting fluorescence from the molecule.

According to another aspect, there is provided a method of sequencing a molecule, comprising a method of the invention and further comprising assigning an identity to each detected fluorescence.

According to some embodiments, the identity is a nucleic acid base. According to some embodiments, the identity is an amino acid.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1A:
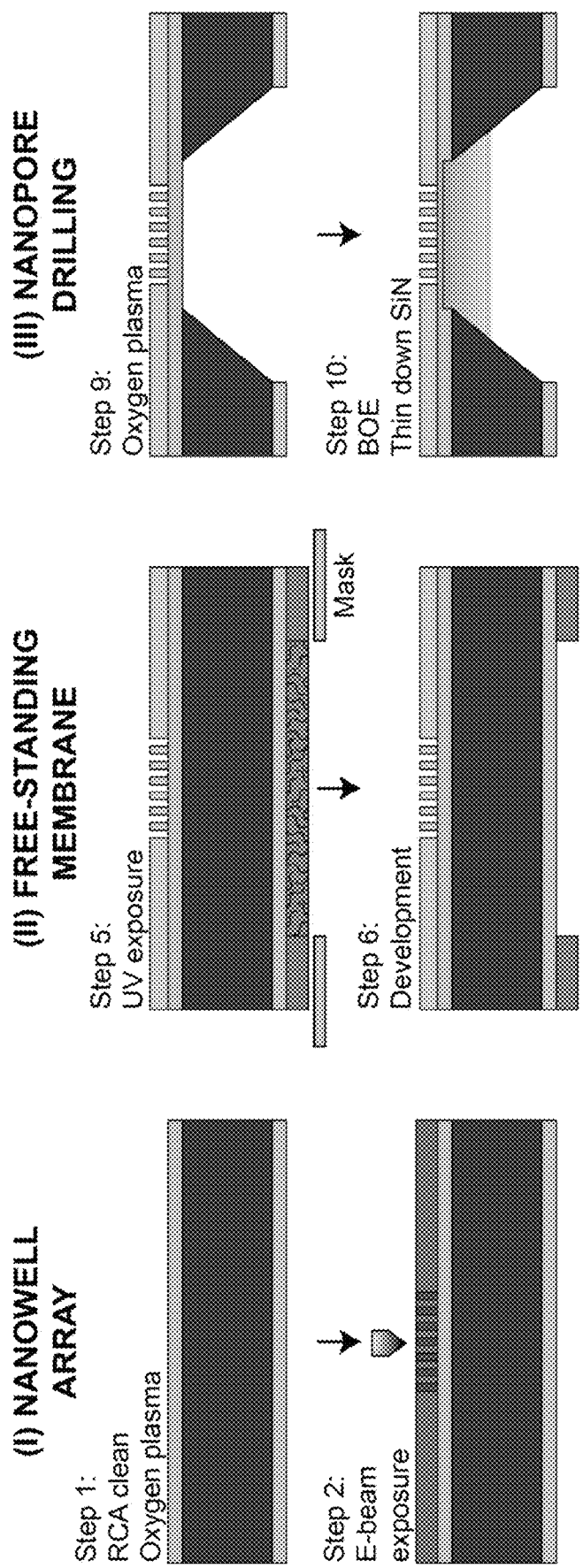
FIGS. 1A-B: Schematic outlines of the full wafer-scale fabrication of PNW-NP chips using negative tone process (1A) and nanopore chips in ultra-thin freestanding SiNx membranes (STD) (1B).
Figure 1A:
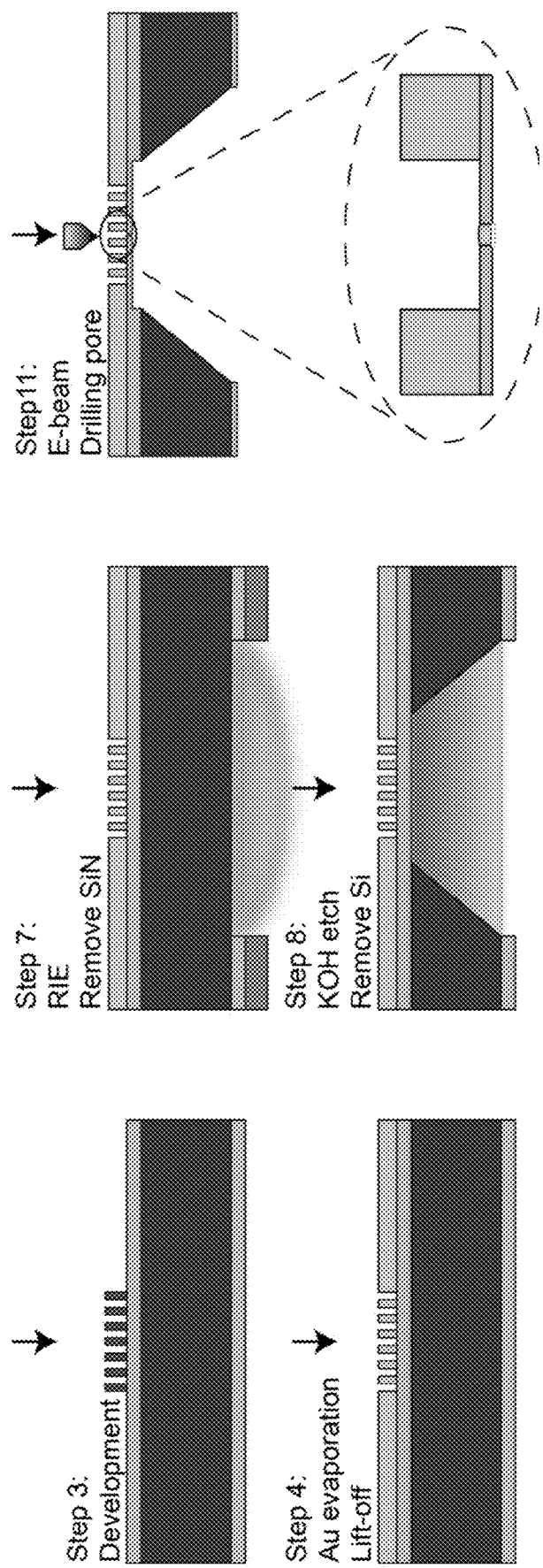

The present invention, in some embodiments, provides systems for detecting fluorescence from a molecule, and methods of using those systems, comprising an ion-impermeable film comprising at least one ion-conducting nanopore; a first and second liquid reservoir separated by the film; a means to induce movement of the molecule from the first reservoir to the second reservoir via the nanopore; a light source capable of exciting the molecule to emit fluorescence, wherein the light source shines into the second reservoir; a metallic layer adhered to the film by an adhesion layer and facing the second reservoir, comprising a nanowell structure located adjacent to the nanopore; and a detector configured to detect the fluorescence emitted by the molecule.

Systems

By a first aspect, there is provided a system for detecting fluorescence from a molecule, the system comprising:
a. an ion-impermeable film comprising at least one ion-conducting nanopore;

b. a first and a second liquid reservoir separated by the film;
c. a means to induce movement of the molecule from the first reservoir to the second reservoir via the nanopore;
d. a light source capable of exciting the molecule to emit fluorescence, wherein the light source shines into the second reservoir;
e. a metallic layer adhered to the film by an adhesion layer, and comprising a nanowell structure located adjacent to the nanopore; and
f. a first detector configured to detect said fluorescence emitted by the molecule.

By another aspect, there is provide a substrate comprising:
a. an ion impermeable film comprising at least one ion-conducting nanopore; and
b. a metallic layer adhered to the film by an adhesion layer, the metallic layer comprising a nanowell structure located adjacent to the nanopore.

By another aspect, there is provided a system for detecting fluorescence from a molecule, the system comprising:
a. a substrate of the invention;
b. a first and a second liquid reservoir separated by the film;
c. a means to induce movement of the molecule from the first reservoir to the second reservoir via the nanopore;
d. a light source capable of exciting the molecule to emit fluorescence, wherein the light source shines into the second reservoir; and
e. a first detector configured to detect said fluorescence emitted by the molecule.

In some embodiments the system is for use in sequencing the molecule. As used herein, "sequencing" refers to determining the sequence of components that make up the molecule. Nucleotide sequencing is well known in the art and consists of determining the order of bases of nucleic acids in a molecule. When the molecule is a DNA molecule the bases will be adenine, cytosine, guanine and thymine. When the molecule is RNA the fourth base will be uracil and not thymine. In some embodiments, artificial bases can be sequenced. When the molecule is a polypeptide the sequence of amino acids is determined. In some embodiments, the sequencing is of naturally occurring amino acids. In some embodiments, the sequencing comprises artificial amino acids.

In some embodiments, the system detects fluorescence with low background from the first liquid reservoir. In some embodiments, the system detects fluorescence with low background from molecules within the first liquid reservoir. In some embodiments, the laser and detector are on the second reservoir side of the film. It will be understood by one skilled in the art, that if many fluorescent molecules are present in the liquid of the first reservoir and they can be contacted by the light from the light source they will produce background that is not from the molecule of interest. Thus, limiting access of the light to the molecules in the first reservoir solves the problem of excess background from as yet unanalyzed molecules. In some embodiments, the metallic layer comprises a thickness sufficient to block light emitted by the light source. In some embodiments, the metallic layer comprises a thickness sufficient to block light shown upon it. In some embodiments, the adherence layer comprises a thickness sufficient to block light emitted by the light source. In some embodiments, the adherence layer comprises a thickness sufficient to block light shown upon it. In some embodiments, the metallic layer and adhesion layer each comprise a thickness sufficient to block light emitted by the light source. In some embodiments, the metallic layer and adhesion layer each comprise a thickness sufficient to block light shown upon it. In some embodiments, the metallic layer and adhesion layer together comprises a thickness sufficient to block light emitted by the light source. In some embodiments, the metallic layer and adhesion layer together comprises a thickness sufficient to block light shown upon it. In some embodiments, at least 50%, at least 55%, at least 60%, at least 65%, at least 70%, at least 75%, at least 80%, at least 85%, at least 90%, at least 95%, at least 97%, at least 99% or 100% of light is blocked. Each possibility represents a separate embodiment of the invention. In some embodiments, at least 95% of light is blocked. In some embodiments, at least 50% of light is blocked.

It will also be understood that as the light source is on the second reservoir side and the nanowell is also on that side the nanopore itself can also act as a barrier for background fluorescence from other molecules. A skilled artisan will understand that detection of the molecule occurs while it is in the nanowell, because the nanopore behind it is narrower than the well and because the molecule itself will be blocking the nanopore, light will not be able, or will be only lowly able, to reach the first reservoir and molecules therein.

In some embodiments, the molecule is an organic molecule. In some embodiments, the molecule is a protein or a nucleic acid molecule. In some embodiments, the molecule is a linearized molecule. In some embodiments, the molecule is a protein. In some embodiments, the molecule is a polypeptide. In some embodiments, the molecule is a nucleic acid molecule. In some embodiments, the nucleic acid molecule is any one of single-stranded DNA, double-stranded DNA, RNA, and cDNA. In some embodiments, the nucleic acid molecule is double-stranded DNA. In some embodiments, the molecule comprises at least one tag. In some embodiments, the molecule comprises at least 1, 2, 3, 4, 5, 6, 7, 8, 9, 10, 20 or 30 tags. Each possibility represents a separate embodiment of the invention. In some embodiments, the tags are covalently coupled to specific biochemical groups along the molecule. In some embodiments, the tags are coupled to specific nucleobases along the molecule. In some embodiments, the tags are coupled to specific amino-acids along the molecule. In some embodiment the tags are evenly spaced along the length of the molecule. In some embodiments, there is a tag at least every 2, 5, 10, 20, 30, 40, 50, 60, 70, 80, 90, or 100 bases of a nucleic acid molecule. Each possibility represents a separate embodiment of the invention. In some embodiments, there is a tag at least every 4 bases of a nucleic acid molecule. In some embodiments, there is a tag at every nucleic acid of a molecule. In some embodiments, there is a tag at least every 1, 3, 5, 7, 10, 15, 20, 25, 30, 35, 40, 45, or 50 amino acids of a polypeptide. Each possibility represents a separate embodiment of the invention. In some embodiments, there is a tag at least every 3 amino acids of a polypeptide. In some embodiments, there is a tag at every amino acid of a polypeptide. In some embodiments, the tag is a fluorescent tag. In some embodiments, the molecule comprises a fluorescent moiety. In some embodiments, the moiety is a tag. In some embodiments, the fluorescent moiety is CY5 or CF640R. In some embodiments, the fluorescent moiety is CF640R. In some embodiments, the fluorescent moiety is CY5. In some embodiments, the molecule fluoresces only when contacted by light from the light source.

As used herein, the terms "peptide", "polypeptide" and "protein" are used interchangeably to refer to a polymer of amino acid residues. In another embodiment, the terms "peptide", "polypeptide" and "protein" as used herein encompass native peptides, peptidomimetics (typically including non-peptide bonds or other synthetic modifications) and the peptide analogues peptoids and semipeptoids or any combination thereof. In another embodiment, the peptides polypeptides and proteins described have modifications rendering them more stable while in the body or more capable of penetrating into cells. In one embodiment, the terms "peptide", "polypeptide" and "protein" apply to naturally occurring amino acid polymers. In another embodiment, the terms "peptide", "polypeptide" and "protein" apply to amino acid polymers in which one or more amino acid residue is an artificial chemical analogue of a corresponding naturally occurring amino acid.

The term "moiety" as used herein refers to a part of a molecule, which lacks one or more atom(s) compared to the corresponding molecule. The term "moiety", as used herein, further relates to a part of a molecule that may include either whole functional groups or parts of functional groups as substructures. The term "moiety" further means part of a molecule that exhibits a particular set of chemical and/or pharmacologic characteristics which are similar to the corresponding molecule, i.e. fluorescence. In some embodiments, a fluorescent moiety is part or all of a fluorescent molecule that retains the ability to fluoresce.

As used herein, the terms "film" and "membrane" are used interchangeably and refer to a thin water-impermeable separation between the first and second reservoirs. In some embodiments, the film is ion-impermeable. In some embodiments, the film comprises silicon. In some embodiments, the film is silicon based. In some embodiments, the film comprises silicon nitride (SiNx). In some embodiments the film comprises a metal oxide. In some embodiments, the metal oxide is selected from aluminum oxide ($AlO_2$), titanium oxide ($TiO_2$), silicon oxide ($SiO_2$) and hafnium oxide ($HfO_2$). In some embodiments, the film is set in a silicon wafer. In some embodiments, the wafer is a crystal orientation wafer. In some embodiments, the wafer is thicker in regions that lack a nanopore. In some embodiments, the wafer provides stability to the separation between the first and second reservoirs. In some embodiments, the wafer comprises a diameter of at least 1, 10, 50, 75 or 100 mm. Each possibility represents a separate embodiment of the invention. In some embodiments, the wafer comprises a thickness of at least 50, 100, 150, 200, 250, 300, 350 or 400 μm. Each possibility represents a separate embodiment of the invention.

In some embodiments, the film has a universal thickness. In some embodiments, the film has a constant thickens across its entire area. In some embodiments, the film has a variable thickness. In some embodiments, the film is thinner in the area of the nanopore. In some embodiments, the film comprises a thickness of less than 500, 450, 400, 350, 300, 250, 200, 150, 100, 75, 50, 25, 20, 15, 10, or 5 nm. Each possibility represents a separate embodiment of the invention. In some embodiments, the film comprises a thickness of less than 100 nm. In some embodiments, the film comprises a thickness of about 25 nm. In some embodiments, the film comprises a thickness of about 10 nm. In some embodiments, the film comprises a thickness of less than 10 nm. In some embodiments, the membrane comprises a thickness of about 25 nm distal to the nanopore and a thickness of about 10 nm proximal to the nanopore. In some embodiments, the membrane comprises a thickness of about 25 nm distal to the nanopore and a thickness of less than 10 nm proximal to the nanopore. In some embodiments, a thin membrane proximal to the pore increases spatial recognition. In some embodiments, a thin membrane proximal to the pore decreases the optical background. In some embodiments, a thin membrane proximal to the pore increases a signal to noise ratio from the molecule. A person skilled in the art will appreciate that the thinner the pore, the fewer the bases in the pore at one instance and thus the greater the spatial recognition of each base of the nucleic acid molecule which also will contribute to decreased background. In some embodiments, the film comprises a thickness that allows light from the light source to pass through the film. In some embodiments, the film allows at least 10%, 20%, 30%, 40%, 50%, 60%, 70%, 80%, 90%, 95%, 97%, 99% or 100% of light to pass through it. Each possibility represents a separate embodiment of the invention.

The production of nanopores in a film is well known in the art. Fabrication of nanopores in thin membranes has been shown in, for example, Kim et al., Adv. Mater. 2006, 18 (23), 3149 and Wanunu, M. et al., Nature Nanotechnology 2010, 5 (11), 807-814. Further, methods of such fabrication of films in silicon wafers, and methods of producing nanopores therein are provided herein in the Materials and Methods section. In some embodiments, the nanopore is produced with a transition electron microscope (TEM). In some embodiments, the nanopore is produced with a high-resolution aberration-corrected TEM or a noncorrected TEM.

In some embodiments, the nanopore comprises a diameter not greater than 1, 2, 3, 4, 5, 10, 15, 20, 15, 30, 35, 40, 45 or 50 nm. Each possibility represents a separate embodiment of the invention. In some embodiments, the nanopore comprises a diameter not greater than 5 nm. In some embodiments, the nanopore comprises a diameter of about 5 nm. In some embodiments, the nanopore comprises a diameter between 0.5 and 10, 0.5 and 15, 0.5 and 20, 1 and 10, 1 and 15, 1 and 20, 3 and 10, 3 and 15, 3 and 20, 5 and 10, 5 and 15, or 5 and 20 nm. Each possibility represents a separate embodiment of the invention.

In some embodiments, the film comprises at least one nanopore. In some embodiments, the film comprises at least 2 nanopores. In some embodiments, the film comprises a plurality of nanopores. In some embodiments, the film comprises an array of nanopores. In some embodiments, the array comprises dimensions of 5×5, 5×10, 5×15, 5×20, 5×25, 5×30, 5×35, 5×40, 5×45, 5×50, 10×10, 10×15, 10×20, 10×25, 10×30, 10×35, 10×40, 10×45, 10×50, 15×15, 15×20, 15×25, 15×30, 15×35, 15×40, 15×45, 15×50, 20×20, 20×25, 20×30, 20×35, 20×40, 20×45, 20×50, 25×25, 25×30, 25×35, 25×40, 25×45, 25×50, 30×30, 30×35, 30×40, 30×45, 30×50, 35×35, 35×40, 35×45, 35×50, 40×40, 40×45, 40×50, 45×45, 45×50, or 50×50 μm. Each possibility represents a separate embodiment of the invention. In some embodiments, the array comprises dimensions of 30 μm by 30 μm. In some embodiments, the nanopores are separated by about 1 μm. In some embodiments, the nanopores are separate by at least 1, 1.5, 2, 2.5, 3, 3.5, 4, 4.5, 5, 6, 7, 8, 9 or 10 μm. Each possibility represents a separate embodiment of the invention. In some embodiments, the nanopores are separated by at least 1 μm. In some embodiments, every nanopore will have a corresponding nanowell. In some embodiments, the detector is configured to detect fluorescence at each nanopore-nanowell. In some embodiments, the detector is configured to detect fluorescence at all nanopore-nanowells. In some embodiments, multiple detectors detect fluorescence at multiple wells.

In some embodiments, the first reservoir is suitable to receive a sample comprising the molecule to be detected. In some embodiments, the second reservoir is suitable for the molecule to pass into after detection. In some embodiments, the reservoirs are the same size. In some embodiments, the first reservoir is larger than the second. In some embodiments, the second reservoir is larger than the first. In some embodiments, the second reservoir is attached to a drainage system for emptying the reservoirs. In some embodiments, the first reservoir holds a volume such that the concentration of molecules in reservoir is not too dilute that molecules infrequently contact the nanopore and not too concentrated that there is crowding and/or blockage of the nanopore. In some embodiments, the first reservoir is configured such that the concentration of molecules in the reservoir is between 1 femtomole and 1 micromole.

In some embodiments, the means to induce movement comprises a means of inducing an electrical current from the first reservoir to the second reservoir. In some embodiments, the means to induce movement comprises a negative electrode within the first reservoir and a positive electrode in the second reservoir and wherein the molecule has a negative charge. In some embodiments, the means to induce movement comprises a positive electrode within the first reservoir and a negative electrode in the second reservoir and wherein the molecule has a positive charge. In some embodiments, the molecule is treated with a substance that provides a charge to the molecule before addition to the first reservoir.

In some embodiments, the light source is in the second reservoir. In some embodiments, the light source shines into the second reservoir. In some embodiments, the light source shines at the nanowell. In some embodiments, the light source is configured such that the light emitted first contacts the molecule while the molecule is in the nanowell.

In some embodiments, the light source produces coherent light. In some embodiments, the light source produces collimated light. In some embodiments, the light source produces coherent and collimated light. In some embodiments, the light source produces a coherent and collimated light beam. In some embodiments, the light source is a laser or light emitting diode (LED). In some embodiments, the light source is a laser. In some embodiments, the light source is a monochromatic light source. In some embodiments, the light source produces red light. In some embodiments, the light source produces light having a wavelength between 640 and 650 nm.

In some embodiments, the power of the light source is at most 100, 95, 90, 85, 80, 75, 70, 65, 60, 55, 50, 45, 40, 35, 30, 25, 20, 25, 20, 15, 10 or 5 microwatts ($\mu W$). Each possibility represents a separate embodiment of the invention. In some embodiments, the power of the light source is at most 10 $\mu W$. A person skilled in the art will appreciate that since the system of the invention increases the fluorescence of the molecule light with a lower power may be used. This may result in decreased background.

As used herein, the term "layer" refers to a thin flat continuous piece of material. In some embodiments, the metallic layer comprises a metallic layer having plasmonic properties. In some embodiments, the metallic layer comprises a metal. In some embodiments, the metal is selected from gold, silver, copper, aluminum and a combination thereof. In some embodiments, the metallic layer comprises at least one layer of metal. In some embodiments, the metallic layer comprises more than one layer of metal. In some embodiments, the more than one layer of metal is layered one on top of the other to create one combined metallic layer. In some embodiments, the metallic layer comprises at least one of gold, silver, copper, aluminum and a combination thereof. In some embodiments, the metallic layer comprises gold. In some embodiments, the metallic layer comprises aluminum. In some embodiments, the metallic layer is a gold layer. In some embodiments, the metallic layer is an aluminum layer. In some embodiment, the metallic layer is composed of multiple layers of metals and/or dielectric materials stacked vertically with respect to the membrane. In some embodiments, the metallic layer is made of gold, silver, copper, aluminum or a combination thereof. In some embodiments, the metallic layer is a homogenous layer. In some embodiments, the metallic layer is a heterogenous layer. In some embodiments, the metallic is a combined layer of gold and aluminum. In some embodiments, a combined layer of gold and aluminum comprises a layer of gold and a layer of aluminum. In some embodiments, the layers of gold and aluminum are stacked vertically with respect to the membrane. In some embodiments, the gold layer is proximal to the membrane. In some embodiments, the aluminum layer is proximal to the membrane. In some embodiments, a combined layer of gold and aluminum is a layer of gold and a layer of aluminum. In some embodiments, the metallic layer is gold. In some embodiments, the metallic layer is aluminum. In some embodiments, the metallic layer is at least 50%, 60%, 70%, 80%, 90%, 95%, 97%, 99%, or 100% gold. Each possibility represents a separate embodiment of the invention. In some embodiments, the metallic layer is 100% gold. In some embodiments, the metallic layer is at least 50%, 60%, 70%, 80%, 90%, 95%, 97%, 99%, or 100% aluminum. Each possibility represents a separate embodiment of the invention. In some embodiments, the metallic layer is 100% aluminum. In some embodiments, the metallic layer is at least 50%, 60%, 70%, 80%, 90%, 95%, 97%, 99%, or 100% gold, aluminum or a combination thereof. Each possibility represents a separate embodiment of the invention. In some embodiments, the metallic layer is 100% gold, aluminum or a combination thereof.

In some embodiments, a combined layer of gold and aluminum is used for an assay with high concentrations of analyte and/or molecules. In some embodiments, a combined layer of gold and aluminum is used for an assay with physiological concentrations of analyte and/or molecules. In some embodiments, a physiological concentration and/or a high concentration is 0.1-100, 0.1-500, 0.1-1000, 0.1-1500, 0.1-2000, 0.1-2500, 0.1-3000, 0.1-3500, 0.1-4000, 0.1-4500, 0.1-5000, 0.1-10000, 0.1-50000, 0.1-75000, 0.1-100000, 0.1-500000, 0.5-100, 0.5-500, 0.5-1000, 0.5-1500, 0.5-2000, 0.5-2500, 0.5-3000, 0.5-3500, 0.5-4000, 0.5-4500, 0.5-5000, 0.5-10000, 0.5-50000, 0.5-75000, 0.5-100000, 0.5-500000, 1-100, 1-500, 1-1000, 1-1500, 1-2000, 1-2500, 1-3000, 1-3500, 1-4000, 1-4500, 1-5000, 1-10000, 1-50000, 1-75000, 1-100000, 1-500000, 5-100, 5-500, 5-1000, 5-1500, 5-2000, 5-2500, 5-3000, 5-3500, 5-4000, 5-4500, 5-5000, 5-10000, 5-50000, 5-75000, 5-100000, 5-500000, 10-100, 10-500, 10-1000, 10-1500, 10-2000, 10-2500, 10-3000, 10-3500, 10-4000, 10-4500, 10-5000, 10-10000, 10-50000, 10-75000, 10-100000, 10-500000, 50-100, 50-500, 50-1000, 50-1500, 50-2000, 50-2500, 50-3000, 50-3500, 50-4000, 50-4500, 50-5000, 50-10000, 50-50000, 50-75000, 50-100000, 50-500000, 100-500, 100-1000, 100-1500, 100-2000, 100-2500, 100-3000, 100-3500, 100-4000, 100-4500, 100-5000, 100-10000, 100-50000, 100-75000, 100-100000, 100-500000, 500-100, 500-1000, 500-1500, 500-2000, 500-2500, 500-3000, 500-3500, 500-4000, 500-4500, 500-5000, 500-10000, 500-50000, 500-75000, 500-100000, 500-500000, 1000-1500, 1000-2000, 1000-2500, 1000-3000, 1000-3500, 1000-4000, 1000-4500, 1000-5000, 1000-10000, 1000-50000, 1000-75000, 1000-100000, 1000-500000, 2000-2500, 2000-3000, 2000-3500, 2000-4000, 2000-4500, 2000-5000, 2000-10000, 2000-50000, 2000-75000, 2000-100000, 2000-500000, 5000-10000, 5000-

50000, 5000-75000, 5000-100000, 5000-500000, 10000-50000, 10000-75000, 1000-100000, or 1000-500000 nm. Each possibility represents a separate embodiment of the invention. In some embodiments, a combined layer of gold and aluminum generates an increased near-field intensity within the nanowell. In some embodiments, a combined layer of gold and aluminum generates an increased fluorescent emission from the molecule. In some embodiments, the increase is as compared to a metallic layer comprising only one of gold and aluminum. In some embodiments, the increase is at least 5, 10, 20, 30, 40, 50, 60, 70, 80, 90, 100, 110, 120, 130, 140, 150, 160, 170, 180, 190 or 200 times greater than an intensity or fluorescent emission. Each possibility represents a separate embodiment of the invention. In some embodiments, a combined layer of gold and aluminum localizes the near-field intensity within the nanowell. In some embodiments, the localization is as compared to a metallic layer comprising only one of gold and aluminum. In some embodiments, the localization of a combined layer is at least 5, 10, 20, 30, 40, 50, 60, 70, 80, 90, 100, 120, 150, 170 or 200 times greater than for a single-layer. Each possibility represents a separate embodiment of the invention In some embodiments, the metallic layer is on the second reservoir side of the membrane. In some embodiments, the metallic layer is on the first reservoir side of the membrane. In some embodiments, the metallic layer is on the first or second reservoir side of the membrane.

In some embodiments, a layer is not composed of freely moving or fixed metallic particles. In some embodiments, the layer is not plasmonic particle within a non-plasmonic substrate. In some embodiments, the metallic layer does not contain non-metallic gaps or voids, such as those created between particles. In some embodiments, the metallic layer is a uniformly flat surface. In some embodiments, the metallic layer is a uniform surface. In some embodiments, the metallic layer comprises a thickness of between 50 and 500, 50 and 450, 50 and 400, 50 and 350, 50 and 300, 50 and 250, 50 and 200, 50 and 150, 100 and 500, 100 and 450, 100 and 400, 100 and 350, 100 and 300, 100 and 250, 100 and 200, or 100 and 150 nm. Each possibility represents a separate embodiment of the invention. In some embodiments, the metallic layer comprises a thickness of between 100 and 150 nm. In some embodiments, the metallic layer comprises a thickness of about 130 nm. In some embodiments, the metallic layer comprises a thickness of at least 30, 40, 50, 60, 70, 80, 90 or 100 nm. Each possibility represents a separate embodiment of the invention. In some embodiments, the metallic layer comprises a thickness of at most 60, 70, 80, 90, 100, 110, 120, 130, 140, 150, 200, 300, 400 or 500 nm. Each possibility represents a separate embodiment of the invention.

As used herein, an "adhesion layer" is a layer of any material that when deposited on a thin substrate (the membrane of the invention) it allows stable bonding of the substrate to the metallic layer. Adhesion layers are known in the art, and examples of such may be found in Aouani et. al., ACS Nano, 2009, 3 (7):2043-2048 for non-limiting example. In some embodiments, the adhesion layer comprises a metal or metal-oxide dielectric metal. In some embodiments, the adhesion layer comprises a transition metal. In some embodiments, the adhesion layer comprises a metal oxide. In some embodiments, the adhesion layer comprises titanium, chromium, or nickel. In some embodiments, the adhesion layer comprises chromium. In some embodiments, the transition layer comprises titanium. In some embodiments, the adhesion layer comprises chromium or titanium. In some embodiments, the adhesion layer comprises any one of chromium, chromium oxide, titanium, and titanium oxide. In some embodiments, the adhesion layer is configured to ensures the adhesion of the metallic layer to the film. In some embodiments, the adhesion layer comprises a thickness of at most 5, 10, 15, 20, 25, 30, 35, 40, 45, or 50 nm. Each possibility represents a separate embodiment of the invention. In some embodiments, the adhesion layer comprises a thickness of at most 10 nm. In some embodiments, the adhesion layer comprises a thickness of about 5 nm. In some embodiments, the adhesion layer comprises a thickness of at least 1, 2, 3, 4, or 5 nm. Each possibility represents a separate embodiment of the invention.

It will be understood by one skilled in the art that the adhesion layer is layered directly only the membrane and that the metallic layer is layer directly onto the adhesion layer. The method of performing such is described herein below. In some embodiments, these layers are on the second reservoir side, facing into the second reservoir, which is the side from which the light comes. Regardless of to which side the layers face, the two layers are configured to block light from the light source from reaching the first reservoir.

As used herein, the term "nanowell" refers to a passage through the metallic layer. A nanowell may also be referred to as a nanoslot or nanoantenna. In some embodiments, the nanowell is circular. In some embodiments, the nanowell is rectangular. In some embodiments, nanowell has a geometric configuration. Geometric configurations include squares, rectangles, circles, ovals, triangles, bowties, rods, cylinders, ellipses, disks, rhombuses and any other shape that may be found by one skilled in the art to confer the plasmonic enhancement to fluorescent imaging of the molecule. In some embodiments, the nanowell also is through the adhesion layer. In some embodiments, the nanowell has a constant diameter. In some embodiments, the nanowell is narrower closer to the nanopore and wider at the surface of the metallic layer. In some embodiments, the nanopore is at the center of the nanowell. In some embodiments, the diameter of the nanowell is not greater than the wavelength of the light emitted by the light source. In some embodiments, the diameter of the nanowell is not greater than half the wavelength of the light emitted by the light source. In some embodiments, the diameter of the nanowell is not greater than half, a third, or a quarter of the wavelength of the light emitted by the light source. Each possibility represents a separate embodiment of the invention. A person skilled in the art will appreciate that by having a diameter that is less than the wavelength the nanowell amplifies the fluorescence from the molecule. This is achieved owing to the close proximity of the edges of the nanowell that enhance plasmon resonance between them, and the attenuation of light within the waveguide aperture which results in more localized excitation. In some embodiments, the nanowell comprises a diameter between 10 and 100, 10 and 150, 10 and 200, 20 and 100, 20 and 150, 20 and 200, 30 and 100, 30 and 150, 30 and 200, 40 and 100, 40 and 150, 40 and 200, 50 and 100, 50 and 150 or 50 and 200 nm. Each possibility represents a separate embodiment of the invention. In some embodiments, the nanowell comprises a diameter of between 30 and 150 nm. In some embodiments, the nanowell comprises a diameter of at least 5, 10, 15, 20, 25, 30, 35, 40, 45, or 50 nm. Each possibility represents a separate embodiment of the invention. In some embodiments, the nanowell comprises a diameter of at most 100, 110, 120, 130, 140, 150, 160, 170, 180, 190, or 200 nm. Each possibility represents a separate embodiment of the invention.

In some embodiments, the nanowell is configured to excite a specific plasmonic resonance. In some embodiments, the nanowell is configured to excite at least one plasmonic resonance. In some embodiments, the nanowell is configured to excite a plurality of plasmonic resonance. It will be understood by a skilled artisan that exciting a specific plasmonic resonance will enhance fluorescence from the molecule at a particular wavelength. Thus, by configuring the nanowell to excite at a given plasmonic resonance the nanowell with enhance fluorescence at a desired wavelength. In some embodiments, the configured nanowell enhances fluorescence at or about the wavelength of the fluorescent moiety of the molecule. In some embodiments, the enhancement is single spectral. In some embodiments, the enhancement is multispectral. In some embodiments, the nanowell comprises a reflective layer. In some embodiments, the configuring is modifying the reflective layer. In some embodiments, the configuring is modifying the adhesion layer.

Different fluorochromes have distinct excitation ranges and emission ranges and the nanowell can be configured to enhance specific fluorochromes. Some non-limiting examples of fluorochromes and their maximum excitation and emission wavelengths (nm) include: 7-AAD (7-Aminoactinomycin D) 546, 647; Acridine Orange (+DNA) 500, 526; Acridine Organe (+RNA) 460, 650; Allophycocyanin (APC) 650, 660; Aniline Blue 370, 509; BODIPY® FL 505, 513; CF640R 642, 662; Cy5® 649, 670; Cy5.5® 675, 694; Cy7® 743, 767; DAPI 358, 461; EGFP 489, 508; Fluorescein (FITC) 494, 518; Pacific Blue 410, 455; PE (R-phycoerythrin) 480 and 565, 575; PE-Cy5 480 and 650, 670; PE-Cy7 480 and 743, 767; Propidium Iodide (PI) 536, 617; and YFP (Yellow Fluorescent Protein) 513, 527. Spectra for fluorochromes can also be found at the following websites: probes.com/servlets/spectra/and clontech.com/gfp/excitation.shtml as well as many others known to those skilled in the art.

Configurations of nanowells to enhance excitation at specific or multiple plasmonic resonances are well known in the art and comprise using particular geometries, dimensions, materials, refractive indecies or a combination thereof. Examples of these geometries, materials and dimensions can be found in Fermamdez-Garcia, et al., Design Considerations for Near-filed Enhancement in Optical Antennas, Contemporary Physics, 2014, and may include for example rod, ellipsoid, bowtie, disk and square geometries; gold, silver aluminum and copper nanowells; as well as diameters measuring about 40, 30, 20, 10 and 5 nm.

In some embodiments, all nanowells of the system comprise the same configuration. In some embodiments, the configuration is a geometric configuration. In some embodiments, a plurality of nanowells of the system comprise the same configuration. The nanowells of the system may be designed such that each nanowell has a different configuration, such that all nanowells have the same configuration or any combination in between. Thus, a first proportion of the nanowells may have a first confirmation, a second proportion of the nanowells have a second confirmation, a third proportion of the nanowells have a third confirmation and so on for as many types of configurations as are desired.

In some embodiments, the metallic layer comprises a plurality of nanowells in a proximity to one another sufficient to generate inter-nanowell plasmonic resonance. In some embodiments, at least 2, 3, 4, 5, 10, 15, 20, 25, 30, 35, 40, 45 or 50 nanowells are in a proximity to one another sufficient to generate inter-nanowell plasmonic resonance. Each possibility represents a separate embodiment of the invention. In some embodiments, a proximity sufficient to generate inter-nanowell plasmonic resonance is between 10-1000 nm. In some embodiments, the proximity is less than 10000, 9000, 8000, 7000, 6000, 5000, 4000, 3000, 2500, 2000, 1500, 1000, 900, 800, 700, 600, 500, 400, 300, 200, 100 or 50 nm. Each possibility represents a separate embodiment of the invention. In some embodiments, the proximity is between 1-5000, 1-4000, 1-3000, 1-2000, 1-1500, 1-1000, 1-900, 1-800, 1-700, 1-600, 1-500, 5-5000, 5-4000, 5-3000, 5-2000, 5-1500, 5-1000, 5-900, 5-800, 5-700, 5-600, 5-500, 10-5000, 10-4000, 10-3000, 10-2000, 10-1500, 10-1000, 10-900, 10-800, 10-700, 10-600, 10-500, 20-5000, 20-4000, 20-3000, 20-2000, 20-1500, 20-1000, 20-900, 20-800, 20-700, 20-600, 20-500, 50-5000, 50-4000, 50-3000, 50-2000, 50-1500, 50-1000, 50-900, 50-800, 50-700, 50-600, or 50-500 nm. Each possibility represents a separate embodiment of the invention. In some embodiments, enhanced inter-nanowell plasmonic resonance enhances fluorescence of a molecule within at least one nanowell in the plurality of nanowells within the proximity. In some embodiments, fluorescence is enhanced in a plurality of nanowells in the proximity. In some embodiments, fluorescence is enhanced in all nanowells in the proximity. In some embodiments, the enhanced fluorescence is at a particular wavelength or plurality of wavelengths. In some embodiments, the enhancement is single spectrum or multispectral.

In some embodiments, the plurality of nanowells in a proximity are evenly spaced apart. In some embodiments, the plurality of nanowells in a proximity are asymmetrically spaced. In some embodiments, the plurality of nanowells in a proximity are spaced in a geometric shape. Examples of possible geometric shapes include, but are not limited to, a circle, a square, a triangle, a rectangle, an oval, a pentagon, a hexagon, a bowtie, an ellipse, and a line. Further examples, of spatial configuration of a plurality of nanowells can be found in Gopinath, et al., Photonic-Plasmonic Scattering Resonance in Deterministic Aperiodic Structures, Nano Letters, 2008 and Langguth, et al., Plasmonic Band Structure Controls Single-Molecule Fluorescence, ACS Nano, 2013.

In some embodiments, the system further comprises a quencher. In some embodiments, the quencher is a dye. In some embodiments, the quencher is at a plasmonic hotspot of a nanowell. In some embodiments, the quencher is outside of the plasmonic hotspot. In some embodiments, the quencher reduces background fluorescence. In some embodiments, the quencher reduces fluorescence outside of the plasmonic hotspot. In some embodiments, the molecule to be analyzed comprises the quencher. In some embodiments, the quencher is proximal to the fluorescent moiety on the molecule. In some embodiments, the quencher increases quantum efficiency. Quenchers in plasmonics are well known in the art. An example of a possible quencher includes but is not limited to methyl viologen, and further examples of quenchers can be found in Wenger et al., Fluorescence enhancement factors on optical antennas: enlarging the experimental values without changing the antenna design, Internat. J. of Optics, 2012, herein incorporated by reference.

In some embodiments, the first detector is configured to detect the fluorescence from the molecule of interest. In some embodiments, the first detector is configured to detect the fluorescence from at least 2 molecules in at least 2 nanowell-nanopores. In some embodiments, the first detector is a fluorometer. In some embodiments, the first detector is a photo detector. In some embodiments, the first detector is an Avalanche Photo Diode detector. In some embodiments, the first detector is configured to also detect ion current flow through the nanopore.

In some embodiments, the systems of the invention further comprise a second detector. In some embodiments, the second detector is configured to detect ion current flow through the nanopore. In some embodiments, the second detector is configured to convert the ion current through the nanopore to a measurable electric current. In some embodiments, the second detector is a high-gain current amplifier. In some embodiments, the means to induce movement comprises a first electrode with the first reservoir and a second electrode with the second reservoir and the high current amplifier is connect to the first and second electrodes. In some embodiments, the first and second detectors are synchronized. In some embodiments, one of the detector and/or both detectors are configured to coordinate a fluorescent signal with an electrical signal.

In some embodiments, the detecting comprises sub-millisecond (ms) resolution. In some embodiments, the detection comprises a high signal to noise ratio. In some embodiments, the detecting comprises the detecting only fluorescence that occurs in close temporal proximity to a change in ion current flow through the nanopore. In some embodiments, the fluorescence and change in ion current flow occur within 1, 2, 3, 4, 5, 6, 7, 8, 9, 10, 15, 20, 25, 30, 35, 40, 45 or 50 ms of each other. Each possibility represents a separate embodiment of the invention. In some embodiments, the fluorescence and change in ion current flow occur within 20 ms of each other. In some embodiments, the fluorescence and change in ion current flow occur simultaneously.

Methods of Use

By another aspect, there is provided a method for detecting fluorescence from a single molecule, the method comprising:
  a. introducing the molecule into the first reservoir of any of the systems of the invention;
  b. inducing the molecule to move from the first reservoir to the second reservoir via the nanopore;
  c. exciting the molecule within the nanowell to emit fluorescence; and
  d. detecting the fluorescence emitted by the molecule;
thereby detecting fluorescence from a single molecule.

By another aspect, there is provided of sequencing a single molecule, the method comprising:
  a. introducing the molecule into the first reservoir of any of the systems of the invention;
  b. inducing the molecule to move from the first reservoir to the second reservoir via the nanopore;
  c. exciting the molecule within the nanowell to emit fluorescence;
  d. detecting the fluorescence emitted by the molecule; and
  e. assigning to each fluorescence emitted by the molecule an identity;
thereby sequencing a single molecule.

In some embodiments, the first reservoir contains a solution suitable for receiving the molecule. In some embodiments, the molecule is dissolved in a solution. In some embodiments, the dissolving solution and the reservoir solution are the same solution. In some embodiments, the dissolving solution and the reservoir solution are different solutions. In some embodiments, the solution is configured to keep the molecule in a linear state. In some embodiments, the solution is configured to retard and/or reduce the formation of secondary structure in the molecule. In some embodiments, the solution is ionic. In some embodiments, the solution is Tris-EDTA (TE) buffer. TE buffer is well known in the art, and any standard TE buffer may be used. In some embodiments, the reservoir solution is a salt solution. In some embodiments, the reservoir solution is saline. In some embodiments, the reservoir solution comprises potassium chloride.

In some embodiments, the detecting comprises sub-ms resolution. In some embodiments, the detecting comprises a high signal to noise ratio. In some embodiments, the metallic layer and/or the adhesion layer blocks excitation of fluorochromes in the first reservoir and reduce background fluorescence in the system. In some embodiments, the nanowell enhances fluorescence. In some embodiments, the nanowell enhances fluorescence as compared to a system without a metallic layer. In some embodiments, the nanowell enhances fluorescence as compared to a system in which the metallic layer is on the opposite side of the membrane from the light source. In some embodiments, the nanowell enhances fluorescence as compared to a system in which plasmonic metal particles are distributed in a non-metallic substrate. In some embodiments, the increase in fluorescence is by at least 2-, 3-, 4-, 5-, 6-, 7-, 8-, 9- or 10-fold. Each possibility represents a separate embodiment of the invention. In some embodiments, the increase in fluorescence is by at least 5-fold. In some embodiments, the increase in fluorescence is by at least 10-fold. In some embodiments, the increase in fluorescence is by about 10-fold. In some embodiments, the detector and/or detectors detect fluorescence and ion current flow and the detector are configured to synchronize fluorescent events and electrical events, wherein only an event detected simultaneously, or nearly simultaneously by fluorescence and electricity is considered detecting fluorescence from the molecule. In some embodiments, nearly simultaneously comprises within 1, 2, 3, 4, 5, 6, 7, 8, 9 or 10 ms of each other. Each possibility represents a separate embodiment of the invention.

In some embodiments, the method of sequencing a molecule comprises any of the methods of detecting fluorescence of the invention and further comprises assigning an identity to each detected fluoresce. In some embodiments, the molecule is a nucleic acid and the identity is a nucleic acid base. In some embodiments, the identity is a naturally occurring base. In some embodiments, the identity is an artificial base. In some embodiments, the molecule is DNA and the identity is one of adenine, cytosine, guanine and thymine. In some embodiments, the molecule is RNA and the identity is one of adenine, cytosine, guanine and uracil. In some embodiments, the molecule is a polypeptide and the identity is an amino acid. In some embodiments, the identity is a naturally occurring amino acid. In some embodiments, the identity is an artificial amino acid. In some embodiments, the identity is one of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine.

As used herein, the term "about" when combined with a value refers to plus and minus 10% of the reference value. For example, a length of about 1000 nanometers (nm) refers to a length of 1000 nm+−100 nm.

It is noted that as used herein and in the appended claims, the singular forms "a," "an," and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements or use of a "negative" limitation.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Various embodiments and aspects of the present invention as delineated hereinabove and as claimed in the claims section below find experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Strategies for Protein Purification and Characterization—A Laboratory Course Manual" CSHL Press (1996); all of which are incorporated by reference. Other general references are provided throughout this document.

Material and Methods

Wafer-Scale Fabrication of PNW-NP and STD Devices

The wafer-scale fabrication process of PNW-NP devices is presented schematically in FIG. 1A and can be broken down into three main processes. These are: (I) Fabrication of gold nanowell array, (II) Fabrication of freestanding SiNx membrane, and (III) nanopore drilling.

(I) Fabrication of gold nanowell array was carried out using 100 mm diameter, <100> crystal orientation, 350 um thick silicon wafers as the underlying substrate (Virginia Semiconductor). The wafers were coated with 25 nm low-stress silicon nitride (SiNx) from both sides using Low Pressure Chemical Vapor Deposition (LPCVD—Tystar). Before any use, the wafers were cleaned in acid and base baths to remove any organic contamination, followed by oxygen plasma for 2 min at 100 W (Plasma-Therm) to remove any remaining moisture on the surface (FIG. 1A, step 1). Following the cleaning process, a 300 nm layer of Ma-N 2403 negative-tone electron beam lithography resist (Micro Resist Technology) was spun on the wafer at 3000 rpm for 45 sec and baked for 1 min at 90° C. on a hot plate. A pattern of nanowell arrays and alignment marks were defined on the resist using electron-beam lithography system (Raith 150) at 30 kV accelerating voltage (FIG. 1A, step 2). The nanowells were exposed as single dots and their sizes were defined by the total dose irradiated onto the resist. After a post-exposure baking at 90° C. for 2 min, the patterns were developed in Ma-D 525 developer (Micro Resist Technology) for 45 seconds, leaving behind arrays of cylindrical columns "pillars" on the surface of the wafer, as illustrated in FIG. 1A, step 3. Then a thin chromium film of 5 nm thick followed by a gold film of 130 nm thick were deposited on the resist pattern by e-beam evaporation system (CHA). Finally, the resist pillars were lifted-off and dissolved away in an 1165 resist strip bath, leaving behind the imprint of the pillars and forming nanowell arrays in the gold film (FIG. 1A, step 4).

(II) For the fabrication of freestanding SiNx membranes, a standard UV photolithography was used to pattern squares and dice lines openings on the other side of the wafer (FIG. 1A, step 5), through which the nitride was etched using reactive ion etch of CHF3 and O2 plasma (FIG. 1A, step 7). The squares were aligned to the pre-fabricated nanowell arrays using a mask aligner (Karl Suss MA6). Finally, the photoresist was stripped, and an anisotropic KOH etch resulted in ~250 chips, each with a ~30 μm×30 μm free-standing SiNx membrane, supports the gold nanowell array (FIG. 1A, step 8).

(III) For nanopore drilling, the 25 nm thick SiNx membranes were thinned down to improve signal-to-noise ratio by controlled buffered oxide etch (BOE), leaving a sub 10 nm thick free-standing membrane in the nanowell base (FIG. 1A, step 10), where pores were later fabricated. Nanopores were drilled using a high-resolution aberration-corrected TEM (Titan 80-300 FEG-S/TEM, FEI) or a non-corrected TEM (JEOL 2010F).

Wafer-Scale Fabrication of STD Devices

Figure 1B:
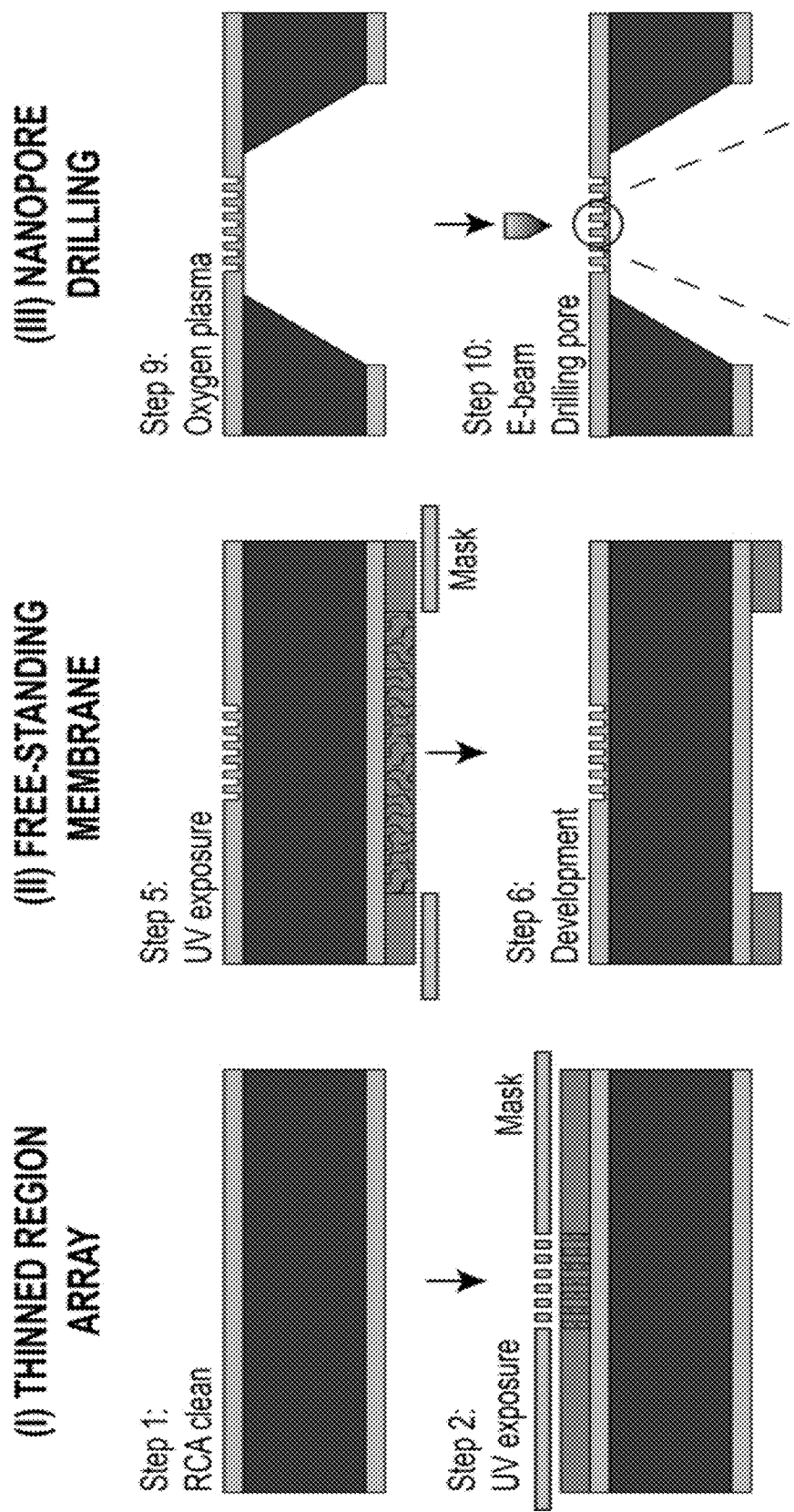
Figure 1B:
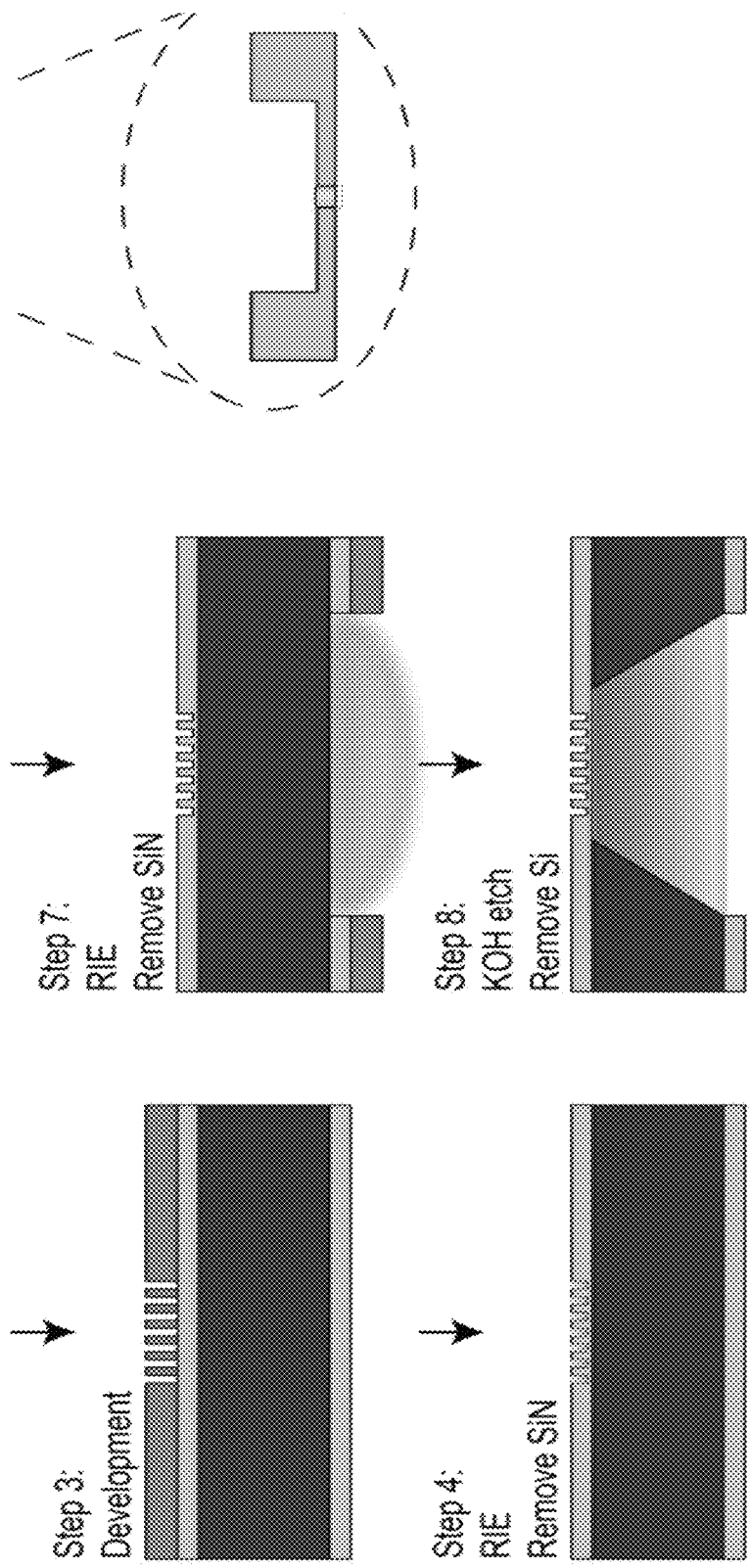

For the control experiments, non-metallic nanopore (STD) devices were fabricated. Briefly, 50 nm thick SiNx membranes were locally thinned down to improve the electrical and optical signal-to-noise ratio by controlled reactive ion etching (RIE) in ~1.5 μm diameter circular regions patterned by full-wafer optical lithography, leaving a sub 10 nm thick wells in which pores were later fabricated using a transmission electron microscope. The wafer fabrication process of the STD devices is illustrated schematically in FIG. 1B.

Experimental Setup

Figure 2A:
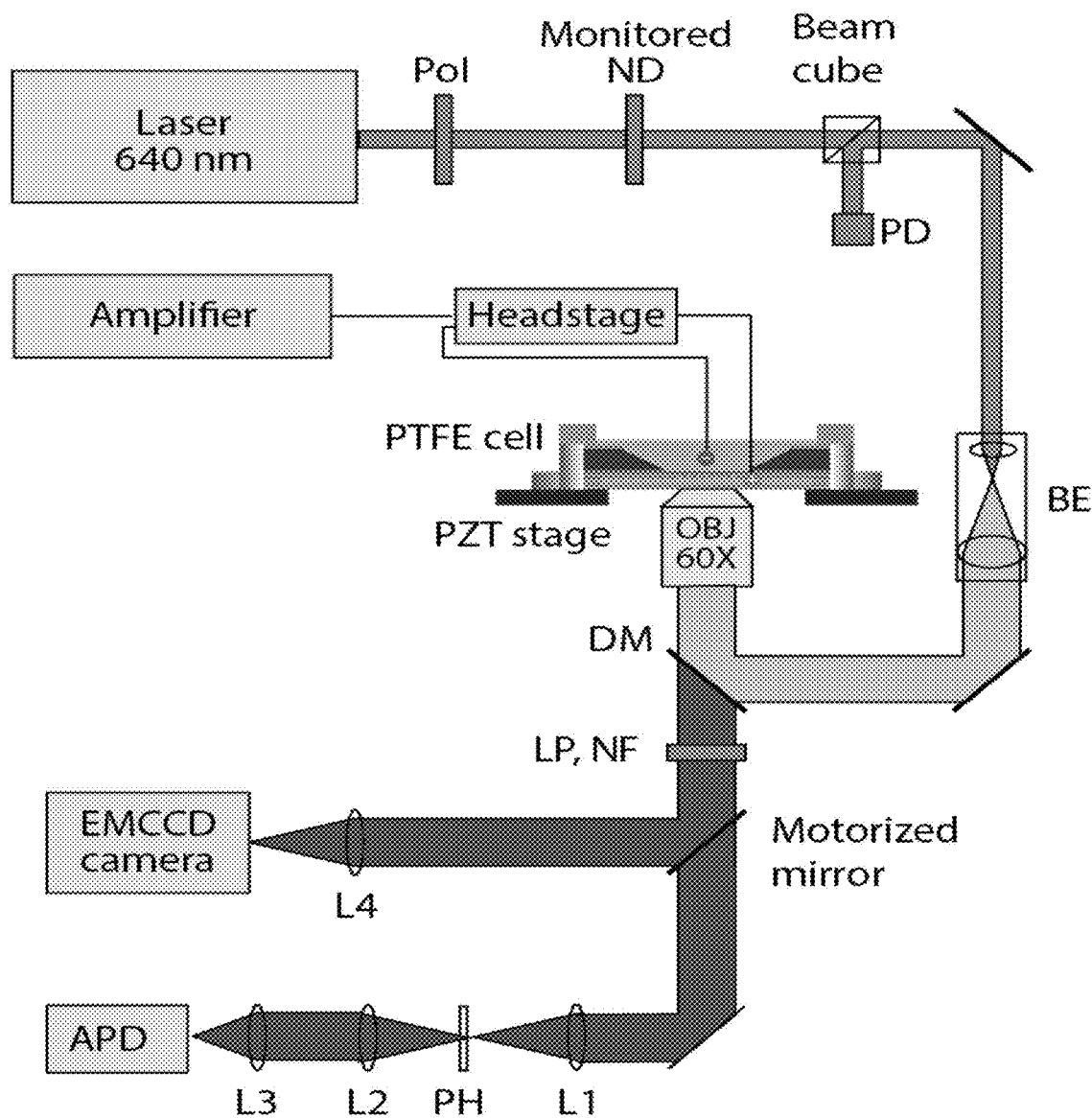
FIG. 2A: A non-limiting schematic illustration of the experimental setup. Abbreviations: Pol, Half-wavelength wave plate; ND, Natural Density; PD, Photo-diode; BE, Beam Expender; DM, Dichroic Mirror; LP, Long Pass; NF, Notch Filter; L, Lense; PH, Pinhole; APD, Avalanche Photo-Diode; PZT stage, Piezo-Nanopositioner; PTFE, Polytetrafluoroethylene.

FIG. 2A displays schematically our optical-electro measurement system. For the synchronous optical and electrical measurements, the nanochip is mounted on a closed-loop XYZ piezo nanopositioner (Physik Instrumente, P 561.3) with sub-nm accuracy on top of a high-NA objective (Olympus Plan Apochromat 60x/1.2) in a custom built confocal setup. A 640 nm solid state laser (QiOptiq IFlex2000) is used for the excitation, and the intensity is adjusted using natural density (ND) filter wheel (Thorlabs FW212CNEB). The laser beam is expanded to completely fill the back aperture of the objective using a custom-made telescope. Emitted light is collected by the same objective and filtered using the appropriate long pass and notch filters (Semrock) and then focused using a single 20 cm focal length lens onto either a EMCCD camera (ANDOR, iXon 887) or to a 50 μm pinhole (Thorlabs) in confocal mode. Light passing through the pinhole is collimated using a 10 cm lens and focused using additional 2.5 cm focal length achromatic doublet lense onto APD (Perkin Elmer SPCM-AQR-14). Back reflection was continuously measured using a photodiode (Thorlabs) to monitor and correct stage or sample drift during the experiment. All lenses were obtained from Thorlabs. The ion current is synchronously measured using two Ag/AgCl electrodes connected to an Axon Axopatch 200B patch-clamp and filtered at 10 KHz. The entire apparatus was shielded from external electromagnetic noise by a Faraday cage. For data acquisition we used National Instruments NI-6211 DAQs for analog signals (sampled at 125 KHz) and NI-6602 for photon counting (sampled at 500 KHz). The two cards were triggered and synchronized via a common hardware connection and were fully controlled by a custom LabVIEW (National Instrument) program.

Fluorescence Intensity Time Traces for Free Florescence Dye

The optical properties of the three device configurations (STD, ZMW, and PNW) were compared by measuring the fluorescence emission from suspensions of freely diffusing dyes (Cy5) over a large range of concentrations, from pM to μM. The set ups were as follows: STD, standard nanochip device, in which the excitation laser forms a diffraction-limited focal spot on the SiNx membrane and the dyes are inserted from the opposite side of the membrane; ZMW, in which the excitation laser is introduced from the $SiN_x$ membrane side and the dyes are inserted at the Au (nanowell) side; and PNW, in which the laser excitation is introduced from the Au (nanowell) side and the dyes are inserted at the $SiN_x$ membrane side (green circles). FIGS. 2C-D clearly shows that in contrast to the STD (blue) and ZMW (red) configurations, the baseline level of the PNW (green) device remains flat as at the water reference level regardless of dye concentration, hence providing nearly ideal baseline for single molecule detection.

Chips Cleaning and Assembly Methods

Figure 3A:
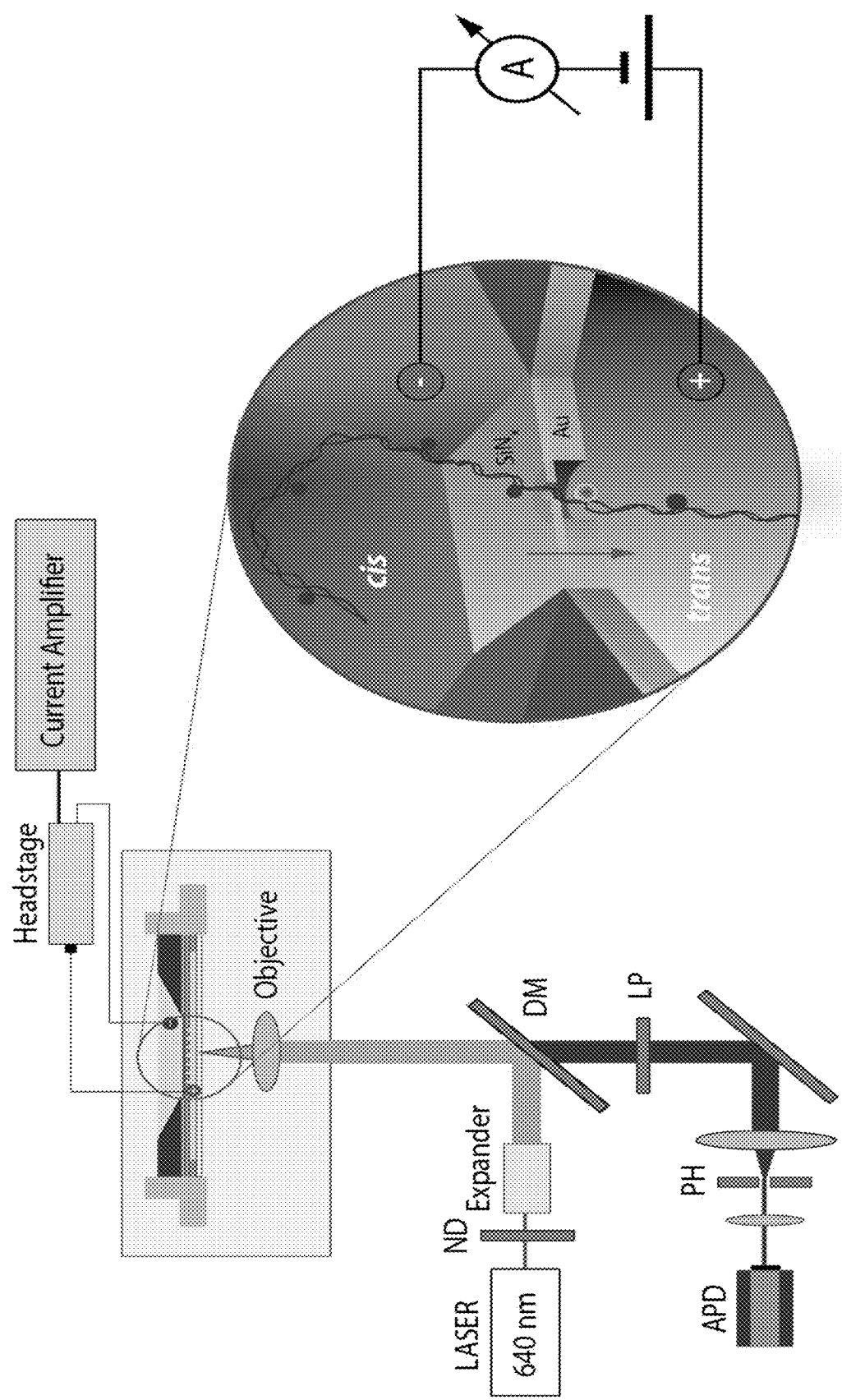
FIGS. 3A-H: Simultaneous electrical and optical recording of DNA translocations through solid-state nanopores. (3A) Upper left panel: A simplified non-limiting illustration of the electro-optical nanopore setup. A collimated laser beam (640 nm) is focused at the nanopore region through the microscope objective lens, forming a tight focus spot for confocal illumination. The emitted photons are directed to an avalanche photo diode. Upper right panel: a non-limiting schematic illustration of the DNA translocation process, in which the ionic current flowing through the nanopore and the fluorescence emissions are probed in a synchronous manner. Entries and transport of labeled DNA molecules are recorded as transitions in the ion current and photon burst. (3B) Back view optical images of the STD and PNW-NP devices. Inset inverted optical microscope images of the membranes, showing the ~1.5 μm thinned region of the STD device and the gold wells of the PNW-NP device. The red arrow indicates the laser spot on the membranes. Green dot lines representing x-scan path. (3C-D) Results from the two scans in the (3C) z and (3D) x directions to obtain optimal nanopore alignment at the confocal spot. (3E-F) Representative electro-optical traces of DNA translocation events recorded using two device configurations: (3E) "STD" and (3F) "PNW-NP". Each panel presents concatenated typical traces of 5 kb DNA covalently labeled with seven CF640R dyes, and a close-up view of a representative single translocation event. Electrical ion current shown in blue and optical signals in red. Asterisks correspond to photon spikes that are not associated with DNA translocations, observed only in the STD device. The optical translocation signal recorded using the plasmonic nanowell-nanopore configuration is enhanced by a factor of 10 as compared to the standard nanochip device configuration. (3G-H) Concatenated typical traces of DNA translocation events (5 kb labeled with seven CF640R fluorophores) recorded using: (3G) an STD device, and (3H) a PNW-NP device.
Figure 3B:
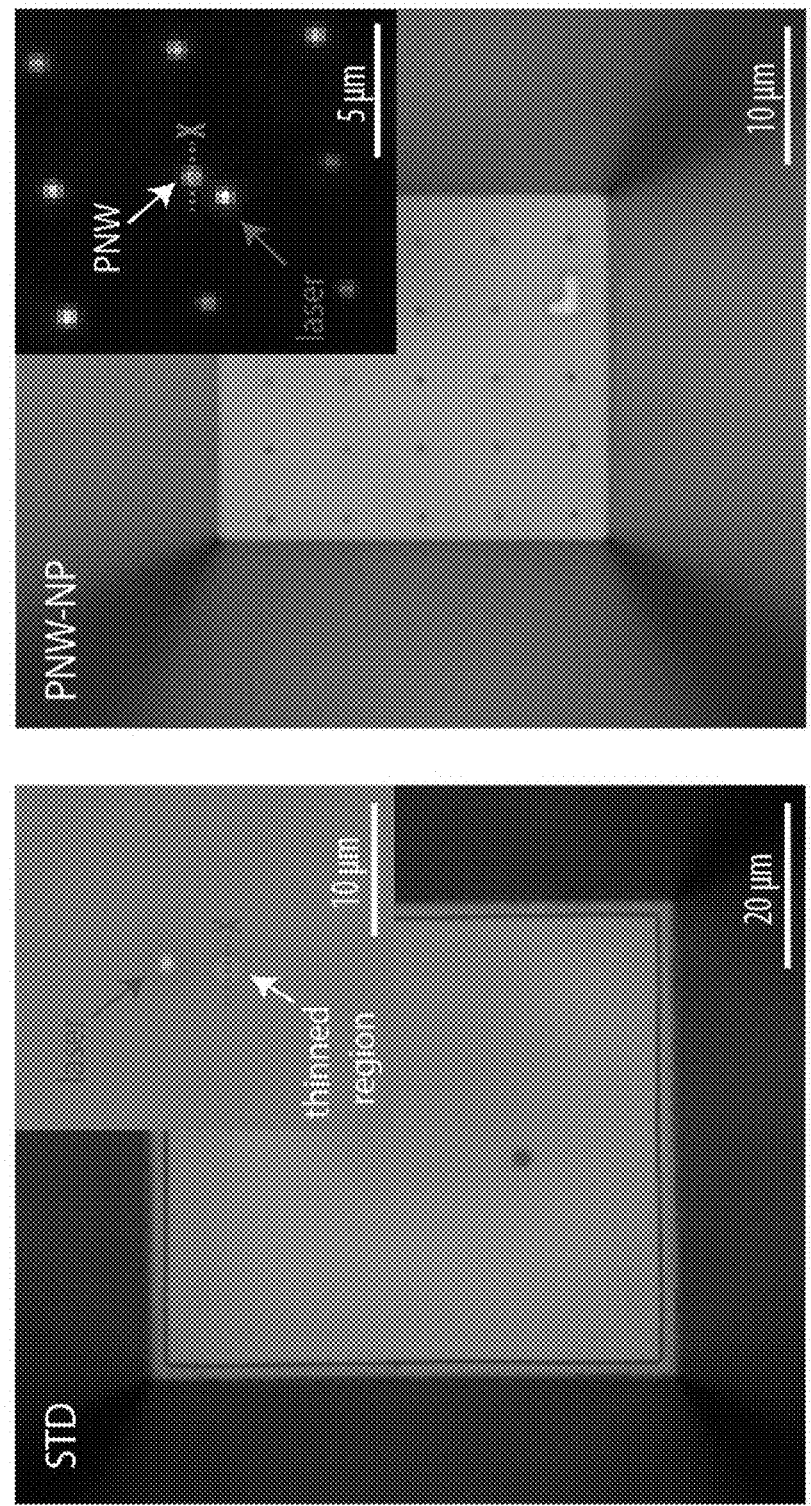
Figure 3C:
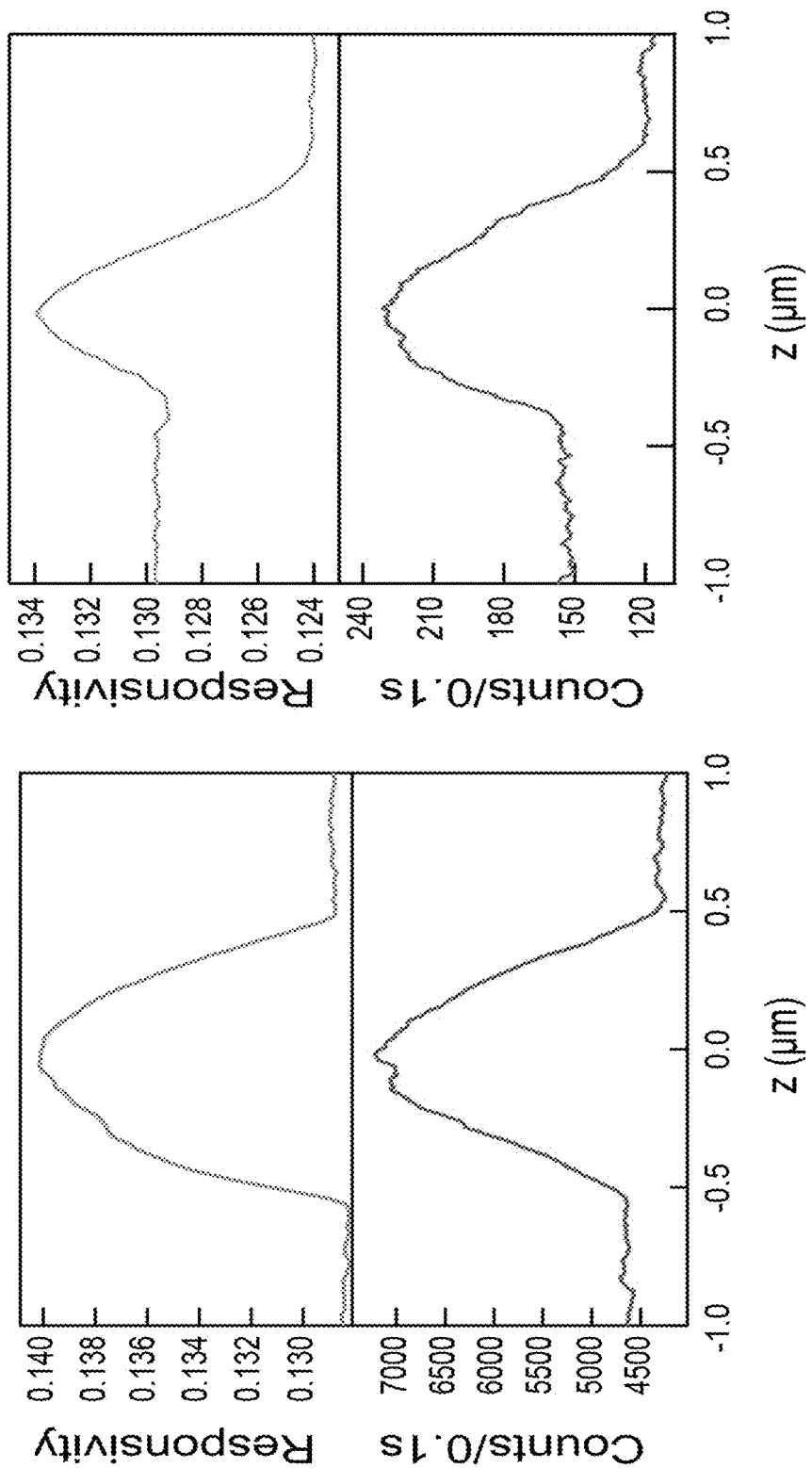
Figure 3D:
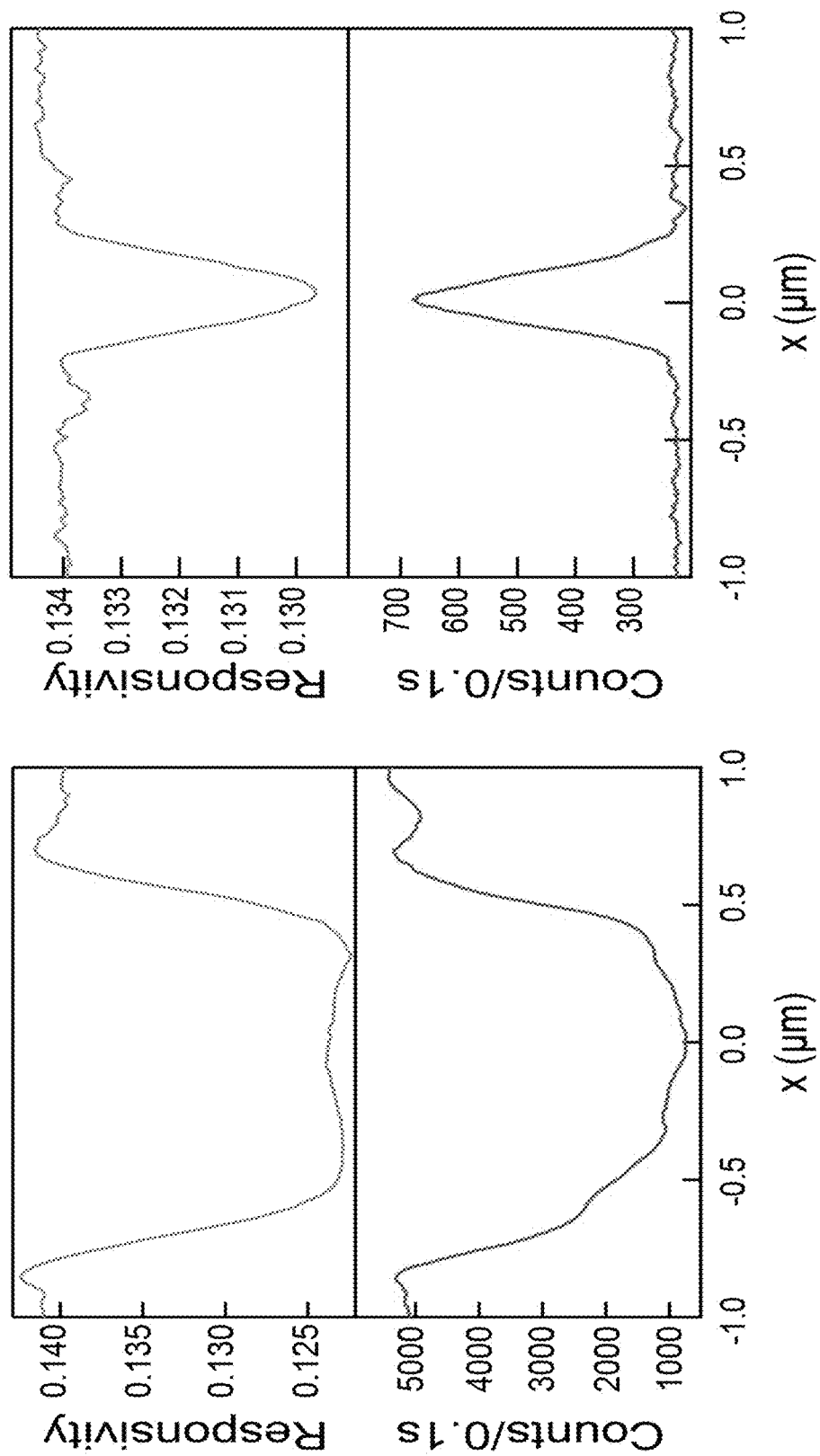

Prior to use in experiments, the nanochip was treated with a low power oxygen plasma to condition the surface (Diener Electronic) and immediately mounted on a custom CTFE cell using silicone rubber (Ecoflex 5 Smooth-ON), giving two independent chambers separated by the insulating SiNx membrane and filled with an electrolytic solution (1 M KCl, 40 mM Tris, 1 mM EDTA, pH 7.2). The CTFE cell was secured to a closed-loop nanopositioner with sub nanometer accuracy, controlled by the LabView program. The nanopositioner was mounted in a custom-built confocal set-up in order to illuminate the nanopore with a focused laser beam, as described herein. Before attempting any optical measurement, an alignment procedure was carefully applied to allow the localization of the nanopore and to determine the optimal alignment of the laser in 3D. The alignment procedure involves 3 main steps. First, a white light illumination was used to coarsely align the membrane and the laser spot as shown in FIG. 3B. In the second step, line scans of the membrane were performed using the nanopositioner and a focused laser beam (640 nm) at a scanning speed of 50 nm/sec, while the emitted photons and reflected light were recorded simultaneously using an APD and a photodiode, respectively. FIG. 3C displays a 2 um line scan through the membrane in the z direction, measured with a laser power of 90 μW for the "PNW-NP" device and 0.9 mW for the "STD" device. In both cases, clear synchronized peaks of the emitted and reflected light were obtained, indicating that the laser focus was aligned with the membrane plane in the z direction. Then the z position was fixed to the value where the highest intensities were detected, and the membrane was scanned in the x-y directions. FIG. 3D displays a line scan in the x direction across the thinned region of the "STD" chip where pore was drilled (scan path is presented by a green dot line. It shows clear reduction of the emitted and reflected light intensities at the thinned region and an additional reduction of the emitted light (photoluminescence) at the region that was exposed to strong e-beam dosage (i.e., pore center). FIG. 3D presents a line scan in the x direction across the gold nanowell where the pore was drilled (scan path is presented by a green dot line). The simultaneous recording of photon emission emanating from the gold coated membrane during the surface scan reveals a pronounced enhancement in photon emission concentric with the area that showed a reduction in the reflected light intensity (i.e., nanowell center). In comparison to the x,y scan measurements of the STD device, the PNW-NP chip shows a higher emitted light intensities in the regions where nanopores were drilled. This is attributed to the fact that surfaces of patterned metal films can be a source of surface plasmon radiation. These particular properties are due to the coupling of light with plasmons on the surface. Finally, a finer alignment was performed by moving the x, y and z coordinates with a step size of 10 nm using the piezo controller, until the position of the laser focus was precisely aligned to the nanopore with nanometric resolution to ensure the best possible performance.

DNA Labeling and Sample Preparation

For DNA labeling, the M. TaqI was used to attach a red fluorophore CF640R (Biotium, Calif., USA) with excitation and emission peaks at 642 nm and 662 nm, to adenine residue in a four base pair sequence TCGA. Labeling is achieved in a single step by feeding the enzyme with a synthetic cofactor containing a fluorophore at the transfer position. A total of 2.5 μg of 5 kbp DNA containing 7 M. TaqI sites (No Limit, Thermo Scientific), was treated with 2.5 μg of M. TaqI and 40 μM of AdoYnCF640R in labeling buffer (20 mM Tris/HOAc, 50 mM KOAc, pH 7.9, 10 mM MgOAc$_2$, 1 mM DTT, 0.01% by volume Triton X-100, 100 μg/ml BSA) in a total reaction volume of 25 μl at 65° C. for 2 h. The labeled DNA was then reacted with 40 μg of protein kinase K (Thermo Scientific) at 45° C. for 1 hr to disassemble protein and DNA aggregates. The reaction was cleaned by ethanol precipitation: 62.5 μl of cold absolute ethanol and 9.6 μl of sodium acetate 3M were added to the reaction, the mixture was incubated for 12 hours at −20.0 followed by centrifugation at 20 k RCF for 1 hr at 4° C. The pellet was washed 5 times in 70% absolute ethanol, vacuum dried and dissolved in TE buffer for UV-Vis absorption quantification and nanopore translocation experiments.

Numerical Simulation Methods

A finite-difference time-domain (FDTD) method was used for the numerical simulations in commercial software, FDTD Solutions, from Lumerical Solutions (Vancouver, Canada). The refractive index of water and SiN$_x$ was taken as 1.33 and 2.1, respectively. The optical constants of gold are known in the art. A uniform mesh size of 1 nm was used to resolve field enhancement of nanometer-sized structures in the simulations. Depending on the symmetry of the simulated structures, we applied anti-symmetric or symmetric boundary conditions to further reduce the simulation times; otherwise, perfectly matched layer (PML) boundaries were used. A plane wave with amplitude of 1 V/m and wavelength range from 400 to 800 nm was used to illuminate the structure by a total-field-total-scattering source. Polarization of the plane wave was perpendicular to the long axis of the NW. A fluorophore was modeled as a classic dipole in the simulation. The near field was recorded with a power monitor. Decay rate and quantum efficiency were calculated by power flow into box monitors surrounding the dipole and PNW-NW structures, by taking the mean of three independent simulations results, wherein a single dipole at the center of the PNW was polarized along the x-, y-, and z-axes respectively.

The fluorescence rate $\gamma_{em}$ of a single molecule can be expressed as a product of excitation rate $\gamma_{exc}$ and quantum yield q,[7, 8]. The fluorescent enhancement is then $$\gamma_{em}/\gamma_{em}^{o}=\gamma_{exc}/\gamma_{exc}^{o} q/q^{o}, \quad \text{(Equation 1)}$$

where superscript 'o' indicates the corresponding free-space quantity, in absence of the PNW. Below saturation, the quantum mechanical decay rate in an inhomogeneous environment is related to the classical power radiated by a dipole in the same environment as $$\gamma/\gamma^{o}=P/P^{o}, \quad \text{(Equation 2)}$$

and the quantum efficiency of an imperfect emitter in a homogenous environment is $$q^{o}=\gamma_{r}^{o}/(\gamma_{r}^{o}+\gamma_{nr}^{o}), \quad \text{(Equation 3)}$$

where $\gamma_r$ and $\gamma_{nr}$ are the radiative and intrinsic non-radiative decay rates. The presence of the PNW structure introduces an additional decay rate $\gamma_{loss}$ due to metallic absorption, and $$q=\gamma_r/(\gamma_r+\gamma_{nr}+\gamma_{loss}), \quad \text{(Equation 4)}$$

assuming intrinsic decay rate is unchanged by environment, $\gamma_{nr}=\gamma_{nr}^{o}$, we can use (Equation 3) and (Equation 4) to express the quantum efficiency enhancement (Equation 1) as $$\eta=P_r/P_r^{o}/[(1-q^{o})+q^{o}(P_r/P_r^{o}+P_{loss}/P_r^{o}), \quad \text{(Equation 5)}$$

The PNW-NP's excitation enhancement is localized to the illuminated gold nanowell. The Au nanowell rapidly attenuates light beyond the aperture, and the planar metallic layers entirely block light from reaching the non-illuminated cis side. The excitation enhancement at the center of aperture is 3.6. Enhancement at this location in our current device of 120 nm diameter NW is near-optimal.

The CF640R (ex./em. 642/662 nm) fluorophore is assumed to have an intrinsic quantum efficiency of $q^{o}=0.3$. Taking this value and results from power flow through the box monitors placed at the center of the PNW into (Equation 5) give a quantum efficiency enhancement at 662 nm of 1.6. It should be noted that if $q^{o}$ is reduced with a quencher the eta of the nanowell is increased according to equation 1. This increase in quantum efficiency of the fluorophore($q/q^{o}$) is achieved without reducing the excitation enhancement which improves the relative fluorescence enhancement of the nanowell.

Electrical and Optical Scatter Plots

Figure 5A:
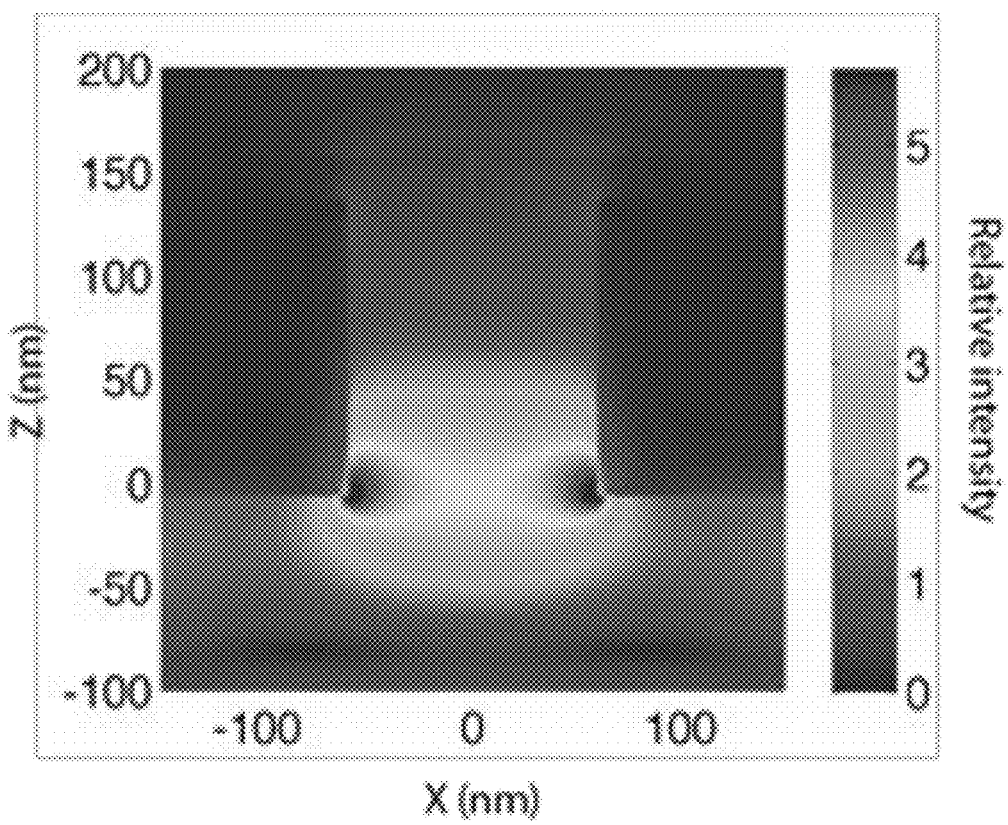
FIGS. 5A-F: Fluorescence enhancement of single molecule translocation through a plasmonic nanowell-nanopore device. (5A-C) Results from Finite-difference time-domain (FDTD) simulations of the device of the invention. (5A) A two-dimensional heat-map of the excitation intensity calculated for a 120 nm PNW-NP device relative to a standard device (no nanowell) illuminated from the gold side. The incoming light (wavelength of 640 nm) is polarized perpendicular to the long axis of the nanowell. (5B) A line graph showing results of a simulation of the excitation enhancement factor as a function of the Au nanowell diameter at 640 nm. (5C) A line graph of the spectrum of the calculated quantum yield enhancement versus wavelength, calculated at the entrance of 120 nm nanowell. (5E-F) Experimental fluorescence enhancement measurements using a 120 nm diameter PNW-NP (4 nm nanopore), compared to standard (STD) device. (5D) Semi-log histograms of the net fluorescence intensity during 5 kbp DNA translocation measured using 9 μW laser power for the STD (blue solid bars) and PNW-NP (gold solid bars) devices. Each DNA is labeled with seven CF640R fluorophores. Histograms of the corresponding background levels measured before the beginning of each event are shown as empty bars. The plasmonic device yield more than a factor of 10 increase in the overall signal to background ratio (S/B). The number of events is indicated in each case. Data is fitted by Gaussian functions (solid lines). (5E) Histograms of DNA translocation events rate for the STD and PNW-NP devices as in 5D, show a six fold larger rate in the PNW-NP case, despite the fact that the background levels are nearly identical, illustrating the background suppression capability of the PNW-NP configuration. (5F) Dot plots showing comparisons between DNA translocation recorded using STD and PNW-NP devices. Left panel displays scatter plots of the optical events amplitude ($I_{Opt}$) versus the optical event dwell time ($t_O$), and the right panel displays scatter plots of the fractional blocked ion current ($I_B$) versus the electrical event dwell time ($t_D$). Measurements were reproduced using the same DNA sample and similar experimental conditions at two different laser intensities: 90 μW and 9 μW.

To quantify the fluorescence enhancement, electro-optical translocation experiments of 5 kbp DNA labeled with seven CF640R fluorophores using both the STD and PNW-NP devices we performed. Each event was analyzed to extract the dwell time and event amplitude for both electrical and optical data traces. FIG. 5F displays the electrical and optical scatter plots of DNA translocations through a 4 nm pore recorded using the custom built confocal setup at either 90 μW or 9 μW laser power. The right panels display the fractional blocked ion current ($I_B$) versus the electrical event dwell time ($t_D$). It clearly shows that the electrical data recorded using the STD device (light blue) as compared to the PNW-NP device (gold) is essentially identical. Specifically, both the blocked ion current and the electrical duration time have a similar distribution for both device configurations. The left panels display the optical events amplitude ($I_{Opt}$) versus the optical dwell time ($t_O$). It shows clear separated distributions that can be discriminated with the optical events amplitude. Specifically, the optical event measured using the PNW-NP device as compared to the STD device yielded a nearly tenfold increase in the event amplitude. Similar magnitude of enhancement was obtained at either 90 uW or 9 uW lase r power, as shown in the FIG. 5F.

Example 1

Generation of a Plasmonic Nanowell-Nanopore (PNW-NP) Device

To create the plasmonic nanowell-nanopore (PNW-NP) devices, a wafer-scale nanofabrication method for manufacturing arrays of subwavelength plasmonic wells in a thin opaque layer of gold deposited on freestanding low-stress silicon nitride membranes was developed. The fabrication process consists of three main steps, described in detail hereinabove in the Materials and Methods section. Briefly, in the first step, a high resolution negative tone patterning was used to define nanopillars of photoresist on the wafer surface, followed by evaporation of 130 nm gold film onto the substrate. The pillars were then dissolved along with the metal on them using lift-off techniques, leading to the formation of nanometric wells in the gold film. In the second step, a hard mask consists of windows and dice lines was opened on the backside of the wafer using Reactive Ion Etching (RIE), followed by anisotropic wet etch of silicon to create a freestanding $SiN_x$ membranes, which overlap with the metallic nanowell arrays. Finally, high-resolution transmission electron microscopy (TEM) was used to fabricate nanopores in the center of the nanowells. Except where stated, the membranes consisted of 25 nm thick freestanding windows of $SiN_x$ approximately 30×30 μm² in size. These membranes were subsequently thinned down using controlled buffered oxide etch (BOE) process, leading to sub 10 nm thick regions in the well base where pores were drilled. This wafer-scale fabrication method results in arrays of precisely controlled and spaced nanowells (FIG. 1A).

Figure 1C:
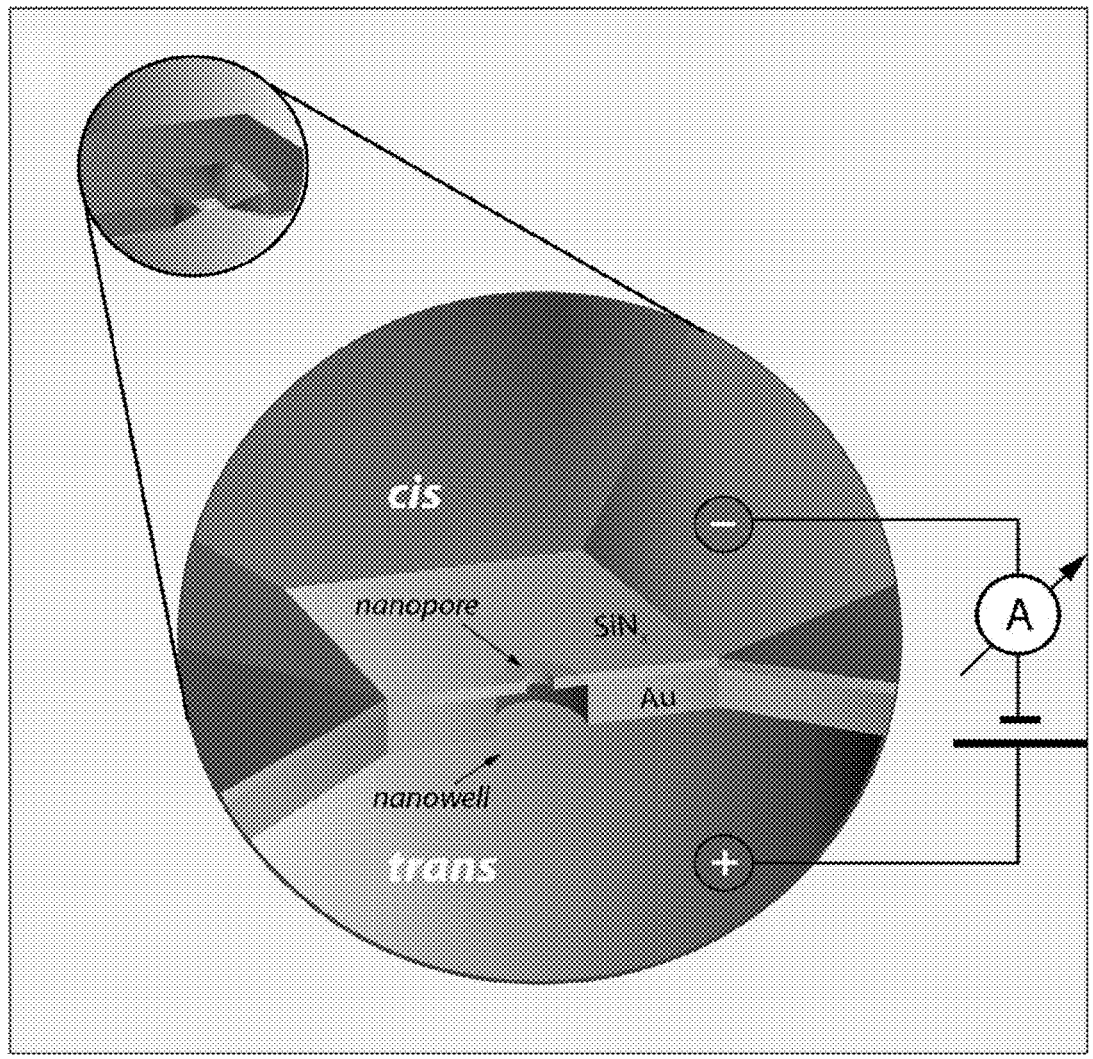
FIG. 1C-G: A plasmonic nanowell-nanopore (PNW-NP) device architecture for enhanced single molecule fluorescence detection. (1C) A non-limiting schematic cross-section of the PNW-NP device containing a nanowell fabricated in a gold film (orange) facing the trans compartment and with a nanopore drilled in the freestanding $SiN_x$ membrane (light green) that faces the cis compartment. (1D) A bright field optical microscope image (back view) of a nanowell array with 5 μm pitch fabricated on ~30×30 μm² freestanding $SiN_x$ membrane. An "L" shape orientation marker (bright pattern on image) is fabricated on each device to facilitate nanowell identification. (1E) A scanning electron microscope (SEM) image (top view) of a typical nanowell with diameter of 120 nm, fabricated in a 130 nm thick polycrystalline Au film. (1F) A transmission electron microscope (TEM) image (top view) of a single nanowell with a nanopore drilled in its base. The bright spot in the center (arrows) correspond to the nanopore. (1G) A high resolution TEM image showing a close-up view of the drilled ~4 nm pore. The bright spot in the center (arrows) correspond to the nanopore.
Figure 1D:
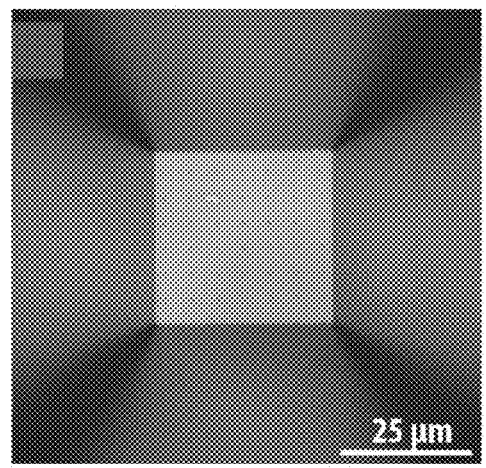
Figure 1E:
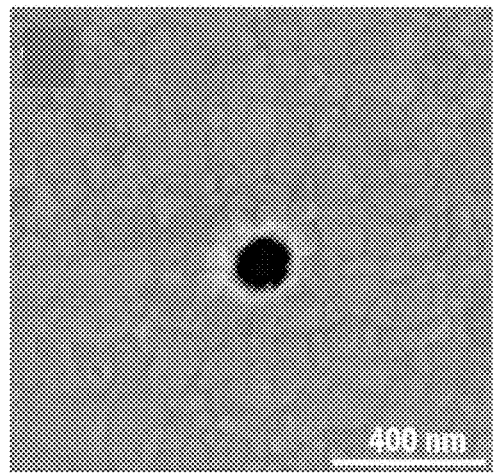
Figure 1F:
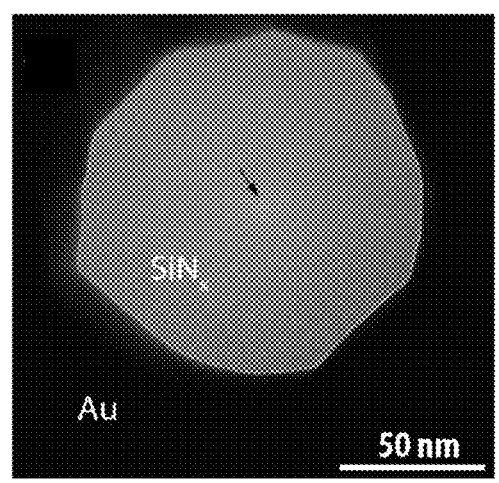
Figure 1G:
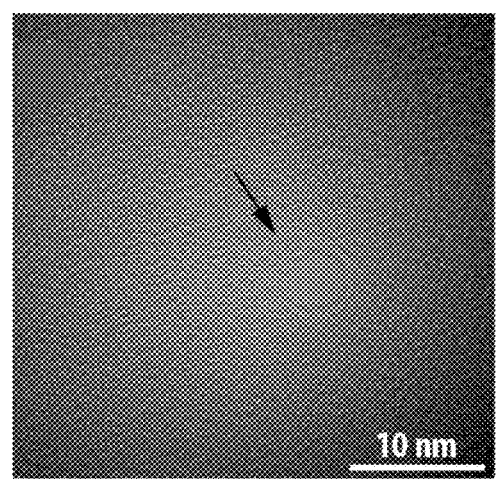

FIG. 1C schematically displays the PNW-NP device. In this illustration the front side of the $SiN_x$ membrane (light green) and the Au layer (orange) are facing down. We conventionally define the cis and trans chambers as the analyte's source and drain compartments, respectively. For negatively charged molecules such as DNA, the trans chamber is positively biased to drive translocation from cis to trans. The fabricated devices were thoroughly characterized using a combination of methods. In the first stage, optical microscopy was used as a high-throughput method to measure variability either within the nanowell arrays or between fabricated devices. FIG. 1D shows an optical bright field micrograph of 7×6 arrays of nanowells with 5 μm interspacing supported by ~30×30 μm² of freestanding $SiN_x$ membrane. The arrays appear to be properly aligned and devoid of any structural defects. In the second stage, scanning electron microscopy was used to characterize the fabricated nanowells. FIG. 1E show scanning electron micrographs of individual nanowell, imaged from the Au side. The magnified image shows the presence of smooth side walls that enables a proper entrance of single molecules inside the nanowell. Finally, high resolution transmission electron microscopy measurements confirmed the physical dimensions and uniformity of the nanowells and the pores drilled in their center. FIGS. 1F and 1G shows transmission electron micrograph of a typical nanowell with 120 nm in diameter that contains a ~4 nm pore at different resolutions.

Example 2

To characterize the optical properties of the PNW-NP device and its ability to suppress background the fluorescence emission from suspensions of freely diffusing dyes (Cy5) over a large range of concentrations, from pM to μM, relevant for single molecule analyses were measured. The measurements were performed using a custom confocal microscope (see Materials and Methods) equipped with an Avalanche Photo Diode (APD) detector for single molecule sensing. Two different configurations of the device were examined: first a "ZMW" (Zero-Mode Waveguide) configuration, in which the excitation laser is introduced from the $SiN_x$ membrane side and the dyes are inserted at the nanowell side. Second, a "PNW" configuration, in which the laser excitation is introduced from the Au (nanowell) side and the dyes are inserted at the $SiN_x$ membrane side. In all cases the emission light is collected in epi-fluorescence mode (same side as the excitation). Additionally, a standard nanochip device ("STD") lacking the Au nanowell was tested. In each measurement the confocal excitation and emission spots were carefully aligned to perfectly overlap with the $SiN_x$ membrane in the z direction and centered in the lateral axes over the nanowell using a nanopositioner, by recording the elastic and non-elastic backscattering, as described hereinabove in the Materials and Methods section. As a reference the background signal from pure $ddH_2O$ sample (filtered using a 0.02 μm syringe filter) for each device configuration was also measured.

Figure 2B:
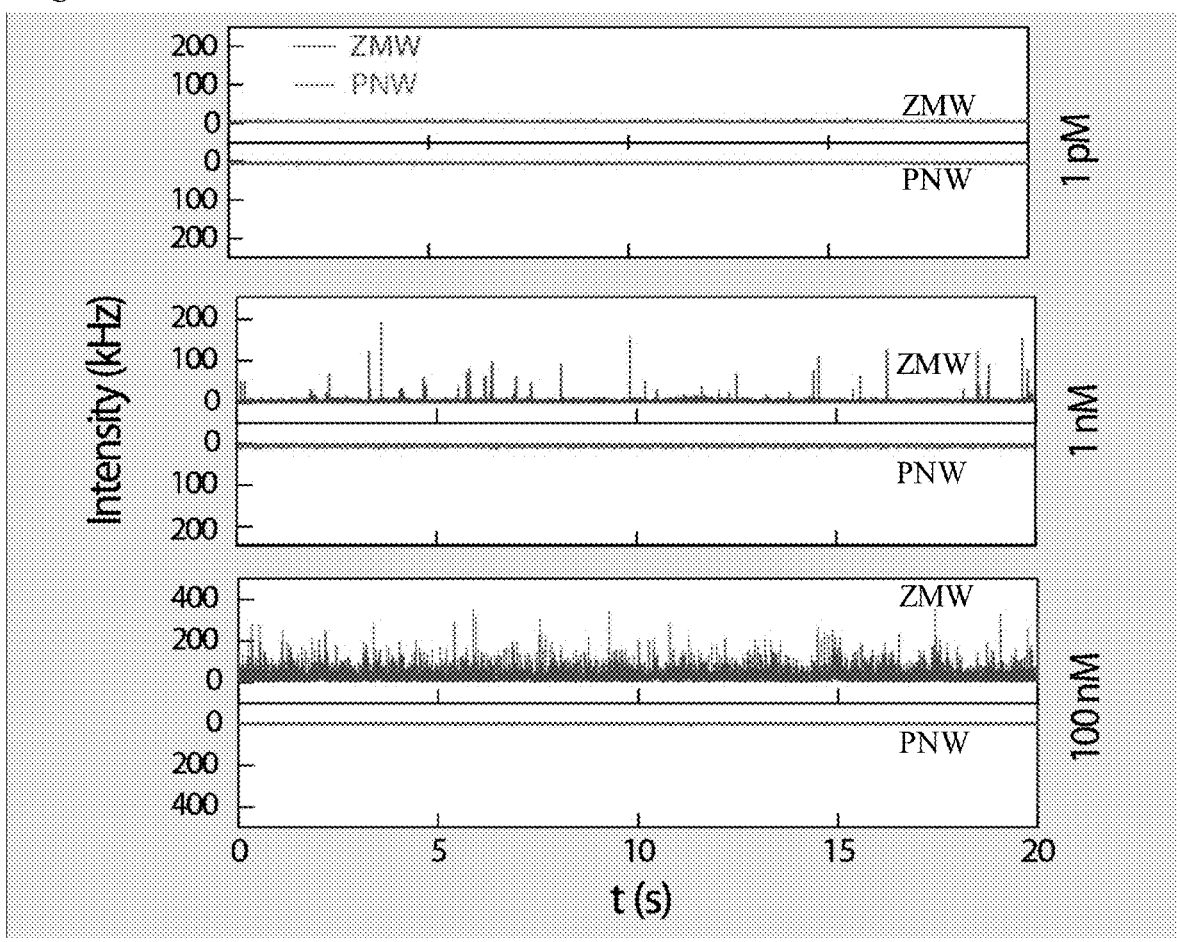
FIGS. 2B-2D: Fluorescence intensity measurements for free florescence dye (Cy5) obtained under red laser excitation (640 nm, 90 uW). (2B-C) Representative fluorescence intensity time traces (raw counts) comparing the (2B) ZMW (red) and PNW (green) and the (2C) STD (blue), ZMW (red), and PNW (green) device configurations with different dye concentrations. (2D) A line graph of normalized photon count rate (intensity) as a function of dye concentration for the three device configurations (inset—schematic of the excitation modes): Data is normalized to the background fluorescence (water solution only) of each device configuration to permit comparison. Lines are guides to the eye.
Figure 2C:
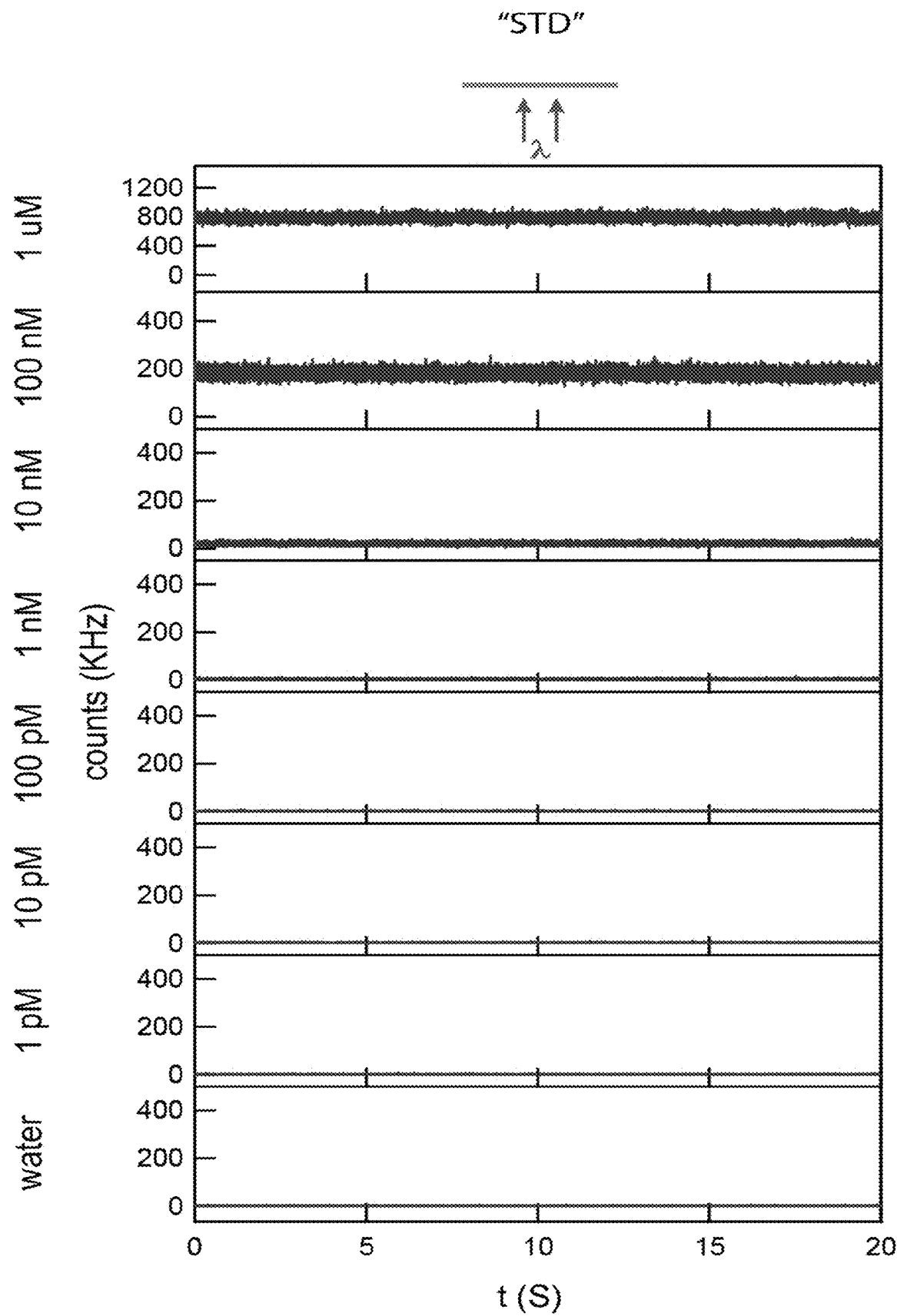
Figure 2C:
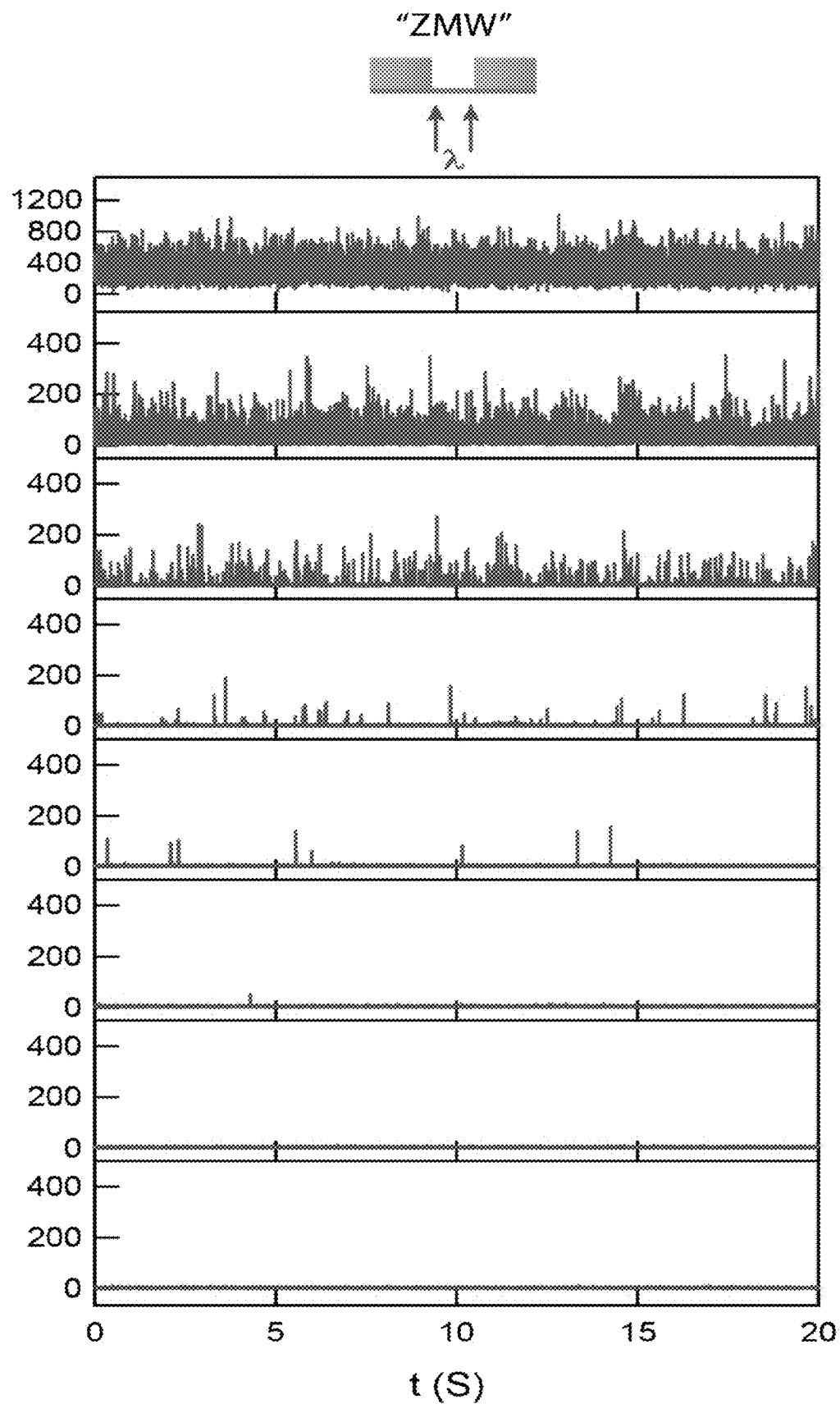
Figure 2C:
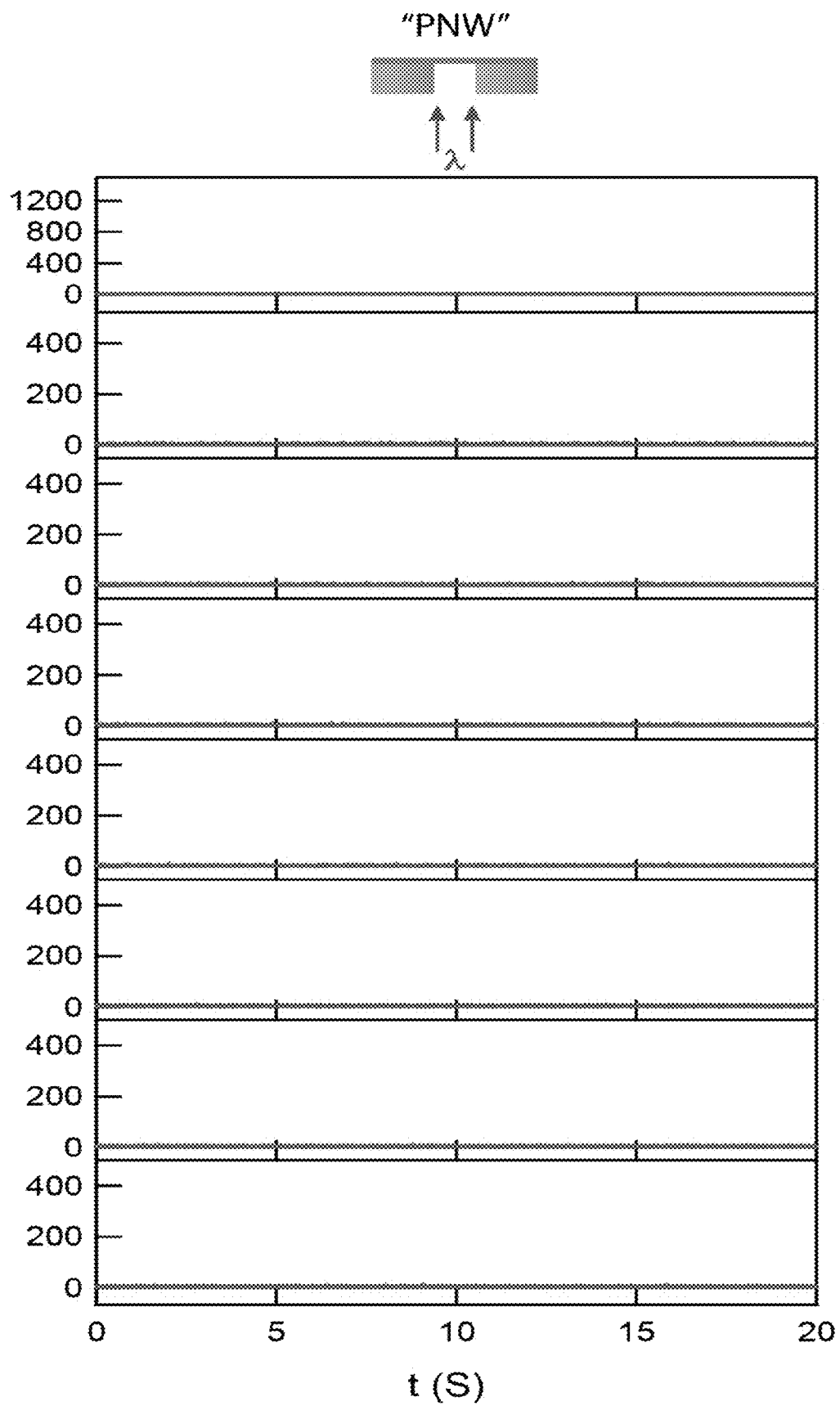
Figure 2D:
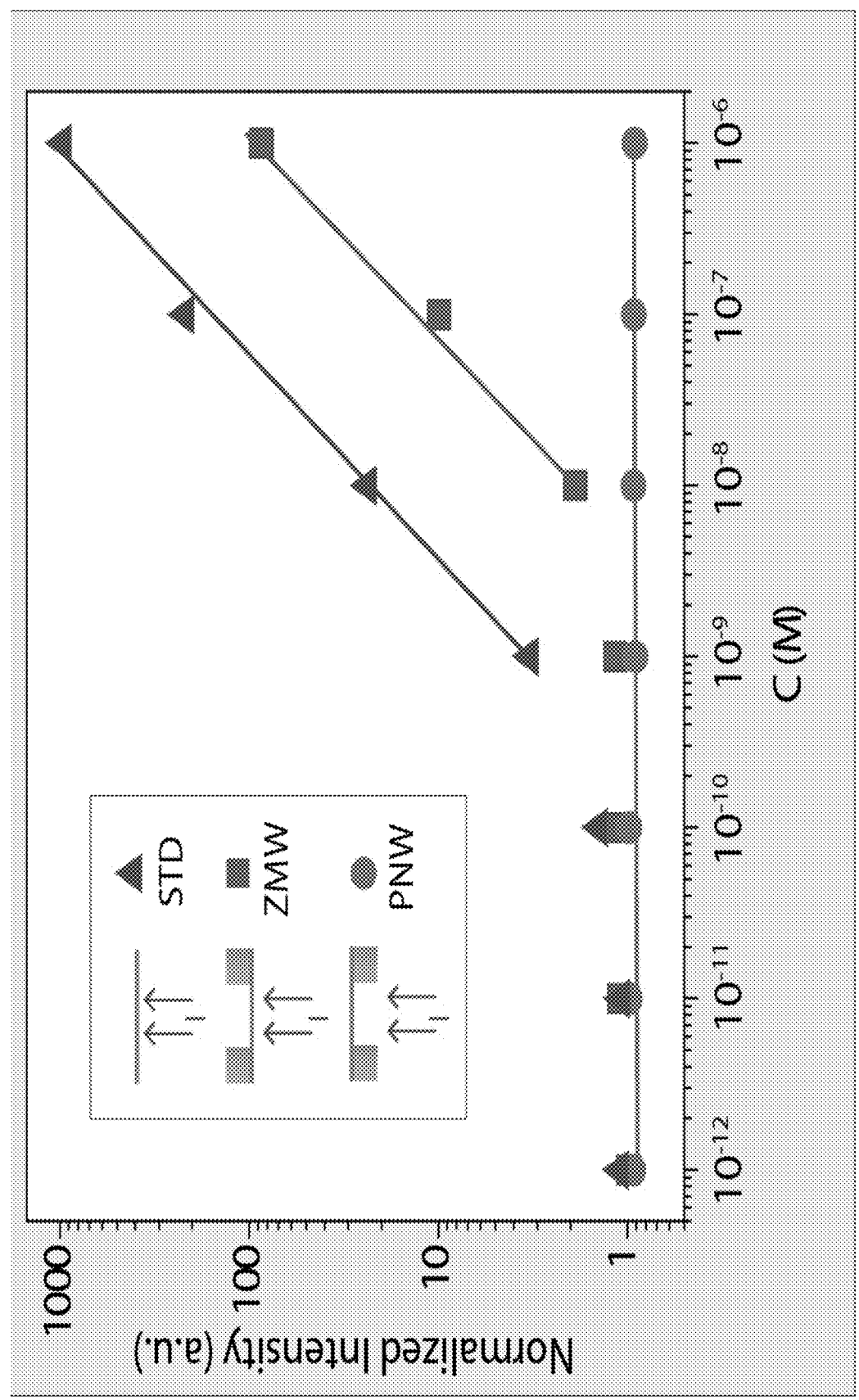

In FIG. 2B representative 20 s time traces of the fluorescence intensities measured using either the ZMW configuration (red lines) or the PNW configuration (green lines) for three different Cy5 concentrations (1 μm, 1 nM and 100 nM) are shown. Additional concentration, as well as a comparison to the STD configuration are provided in FIG. 2C. At the lowest concentration (1 pM) all configurations show flat traces with an average value equal to the reference level. At 1 nM single-molecule bursts are observed in the ZMW trace, but not in the PNW configuration. These bursts represent single molecules sporadically entering the nanowell volume. At 100 nM an increase in the baseline level of the ZMW and STD configurations was observed, but the PNW configuration level remains flat as was observed at the reference level. These results indicate that even at high dye concentration background emission light does not "leak" through the Au layer or the nanowell. Importantly, the apparent background level of the PNW configuration remains at the water reference level regardless of dye concentration, hence providing nearly ideal baseline for single molecule detection.

To characterize the net fluorescence background in each of the configurations, the average emission intensity for each Cy5 dye concentration was measured and normalized by the reference to obtain the net fold increase relative to ultra-pure water. The results are summarized in FIG. 2D, where the average emission as a function of Cy5 concentration from 1 pM to 1 μM is shown. Focusing first on the STD device (blue markers), at extremely low dye concentrations an averaged baseline background level of 1, is observed as expected, but above roughly 0.1 nM there was observed a linear increase of the intensity with Cy5 bulk concentration increase (solid line). Above this concentration single fluorophore detection is practically unfeasible due to the presence of more than a single molecule in the confocal volume (roughly 0.05 fl). The ZMW configuration (red symbols) greatly improves this situation as the Au layer block the excitation in the top chamber, and hence it effectively reduces the observation volume to a fraction of the nanowell volume (i.e. <1.5 Atto-liter), allowing single molecule measurements to take place up to ~100 nM. Finally, the PNW configuration (green symbols) does not appear to be affected by the Cy5 concentration and remains at the baseline level for the entire concentration range tested.

Example 3

Taking advantage of the extremely low optical background level obtained in the PNW configuration it was hypothesized that it would be possible to electrophoretically draw and detect individual, labeled, molecules through the nanowell. Presumably this can be achieved by drilling a nanopore at the bottom $SiNx$ membrane of the nanowell that acts as a "gate", hence sending individual analytes into the nanowell. Moreover, by measuring the ion current flowing through the nanopore precise electrical time gating signals can be obtained for the translocation of each molecule. Since the nanopore can only accommodate one analyte molecule at a time, it circumvents crowding of multiple molecules in the nanowell sensing volume.

To check this hypothesis, an electro-optical sensing apparatus was constructed for the simultaneous detection of the ion current flowing through the nanopore ($I_E(t)$) and the optical photon flux ($I_O(t)$) emitted in the device. This system involves a custom-made stage-scanning confocal microscope with a high numerical aperture water immersion objective (N.A.=1.25), described schematically in FIG. 3A. Briefly, a PNW-NP device is mounted in a special fluidic cell, which on one hand forms two electrically separated fluid chambers ('cis' and 'trans' chambers), and on the other hand is equipped with a bottom quartz cover slide for low-background single-molecule epi-fluorescence excitation/emission. The cell is placed in a nanopositioner stage for precise alignment of the device with the tightly focused laser spot and the optically conjugated confocal volume. To ensure perfect alignment, the system also includes a photodiode, located at a conjugated plane to the focal spot for the detection of the backscattered light. Alignment is obtained when both the backscattered light and the photoluminescence (originated from the SiNx membrane) reach their corresponding minima/maxima in x, y and z directions. The alignment procedure of the PNW-NP is described in detail in the Materials and Methods (FIG. 3B-D).

Figure 3E:
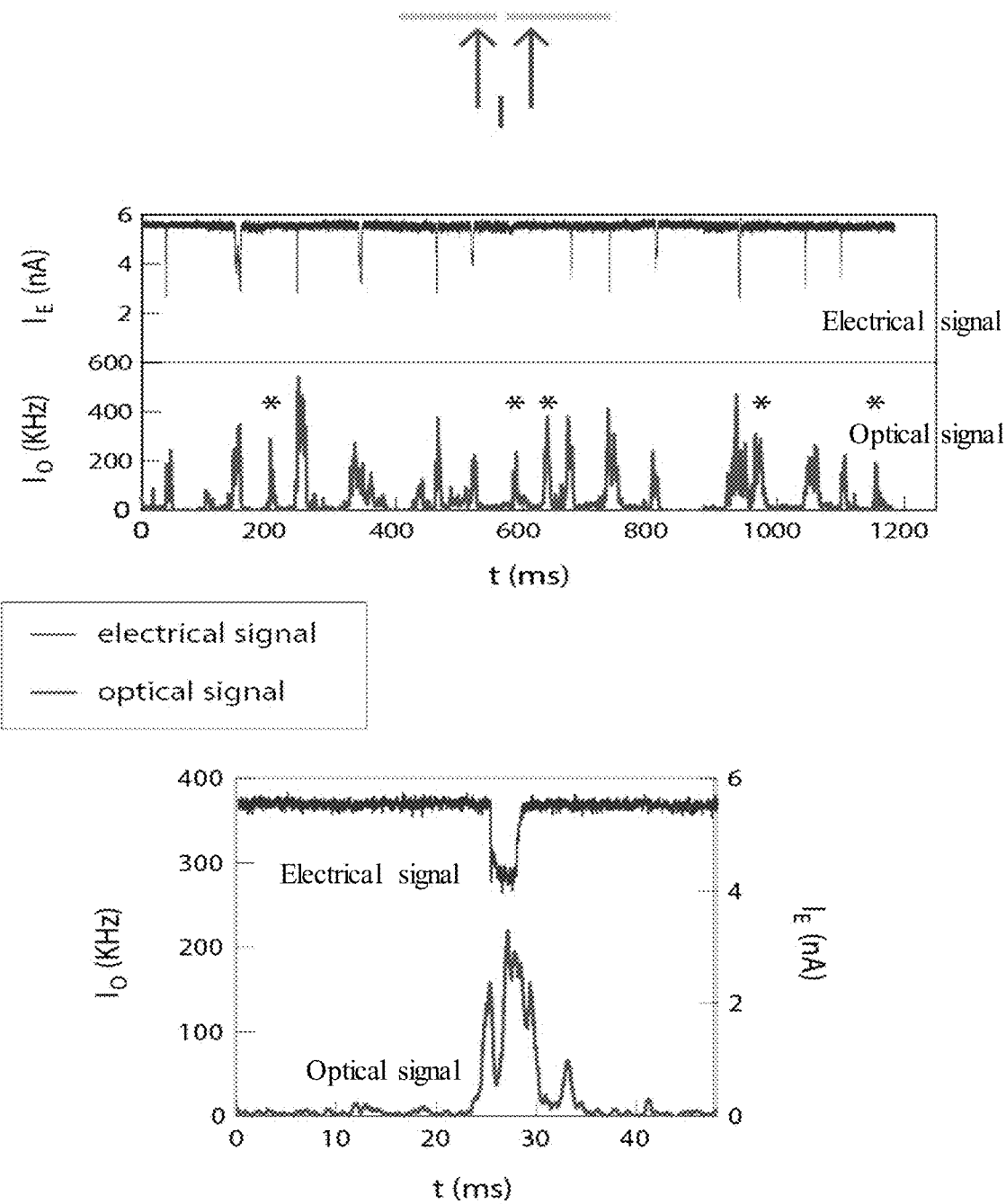
Figure 3F:
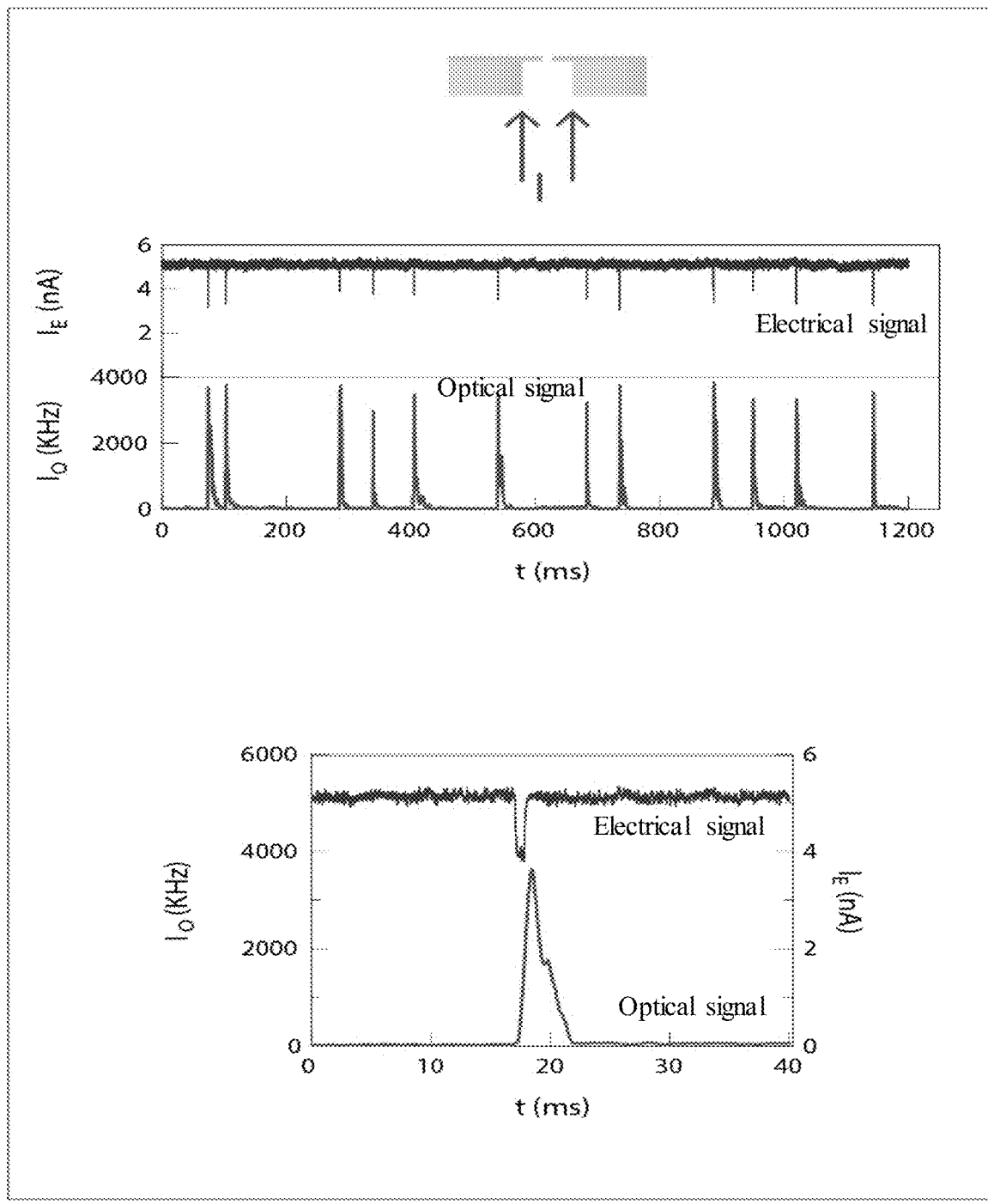
Figure 3G:
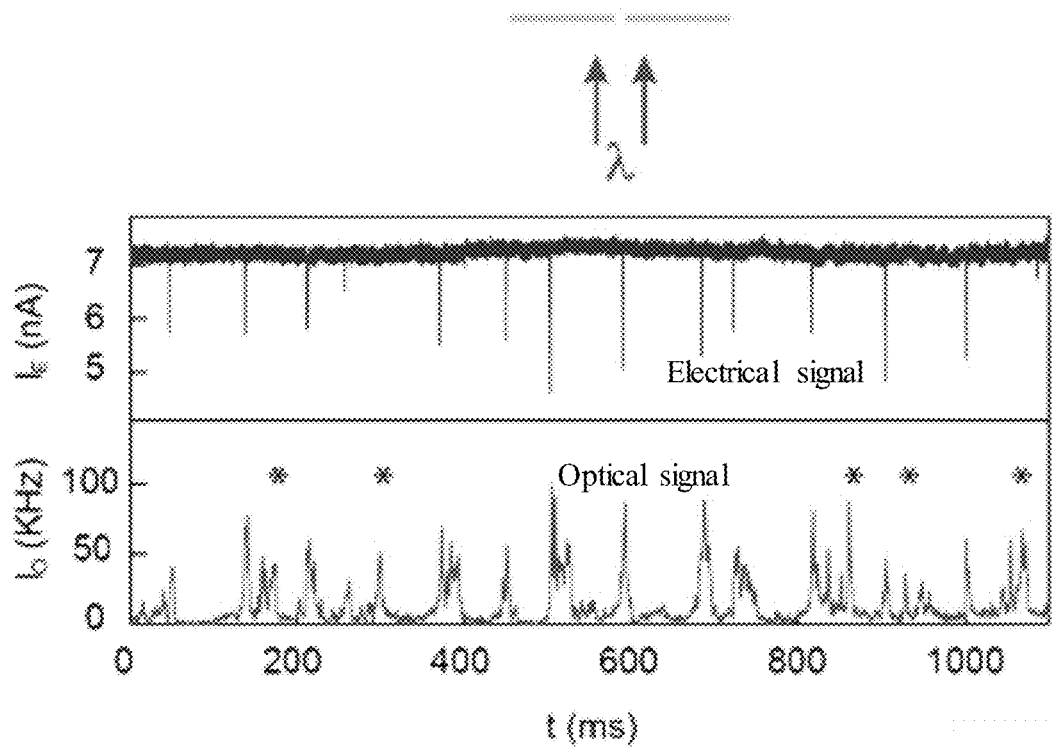
Figure 3H:
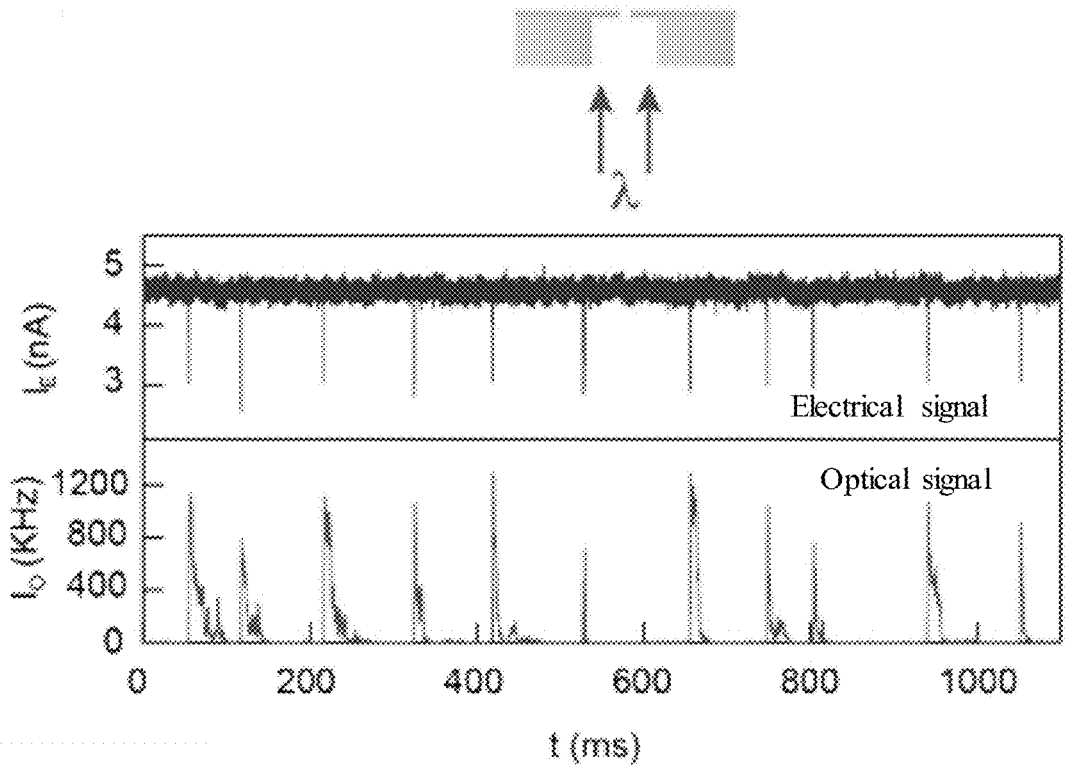

To characterize the electro-optical properties of PNW-NP we labeled a 5 kilobase double stranded DNA molecules with the high-brightness fluorophore CF640R (Biotium, USA, ex./em. 642/662 nm), as explained in the Materials and Methods. Each DNA molecule harbors 7 fluorophores covalently conjugated to an Adenine residue at the specific sequences (5'-TCGA-3') using methyltransferase reaction. The labeled DNA molecules were introduced to the cis chamber at relatively low concentration (10 pM or less) for electro-optical translocation measurements. The device is first aligned with the laser to obtain stable open pore current, after which DNA is introduced. Typical concatenated sets of events collected either using the STD device (no nanowell) or the PNW-NP device are shown at the top panels of FIGS. 3E and 3F, respectively (FIGS. 3G and 3H as well). In each case the electrical and optical signals (blue and red lines respectively) were measured simultaneously. The laser power (set to 90 µW at the back aperture of objective) and other experimental conditions were unchanged. Looking at FIGS. 3E-3H, one can note three salient differences: first and foremost, a nearly tenfold increase in the peak intensities of the events acquired with the PNW-NP device as compared with the STD device is observed. This apparent enhancement in the detected fluorescence intensity is further analyzed in FIG. 5A. Second, in the STD device about 16% of all optical events (N=493) lack a corresponding electrical resistive pulse (an electrical event), as marked with black asterisks in FIGS. 3E and 3G. In contrast, all the optical events in the PNW-NP device (N=272) are accompanied with an electrical resistive pulse. Third, a closer analysis of the time delay between the rise of the optical and electrical events reveals that in the case of the STD device, most of the optical signals begin prior to their corresponding electrical events, but in the PNW-NP device the signals appear to be nearly synchronized. This pattern is exemplified in the zoom-in views of two representative events shown in bottom panels of FIGS. 3E and 3F.

Example 4

Figure 4A:
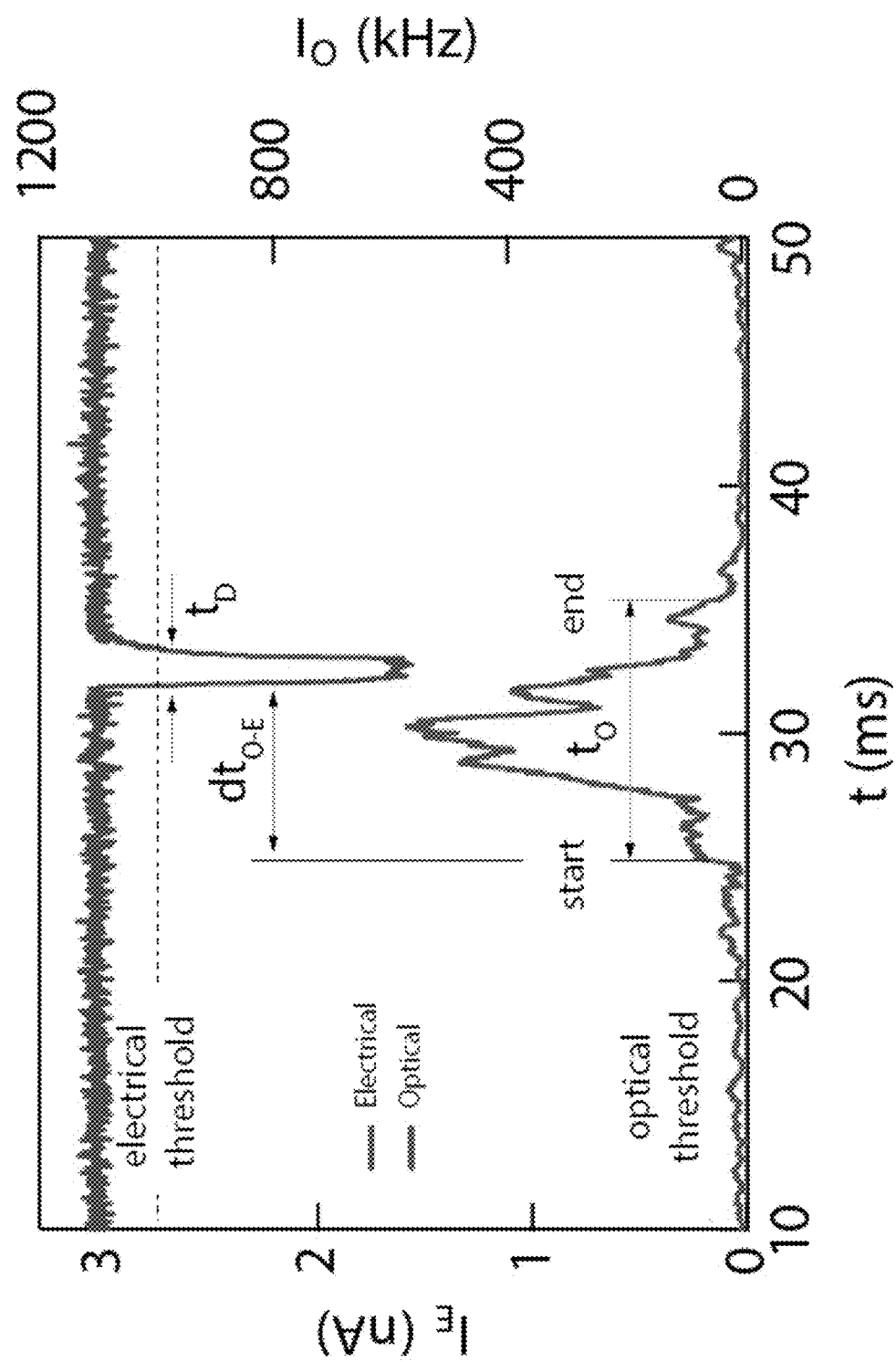
FIGS. 4A-C: Analysis of the optical and electrical translocation dynamics. (4A) Zoom-in view of a typical DNA translocation event (STD device). Thresholds set at 3 standard deviations away from baseline levels for both the electrical and optical signals (dashed lines) were used to extract the electrical dwell time ($t_D$) the optical dwell time ($t_O$), start time ($t_{start}$) and end time ($t_{end}$) of the electrical and optical events. (4B) Histograms showing distributions of $t_D$ measured using STD device (light blue bars) and PNW-NP device (inset—gold bars). The data are fitted by exponential functions (solid lines). (4C) Histograms showing distributions of the time delay between the rise of the optical and electrical signals ($\delta t_{O-E}$) measured using STD device (light blue bars) and PNW-NP device (gold bars). The number of events is indicated in each case. In the PNW-NP device the start time of the electrical and optical times are practically synchronized.
Figure 4B:
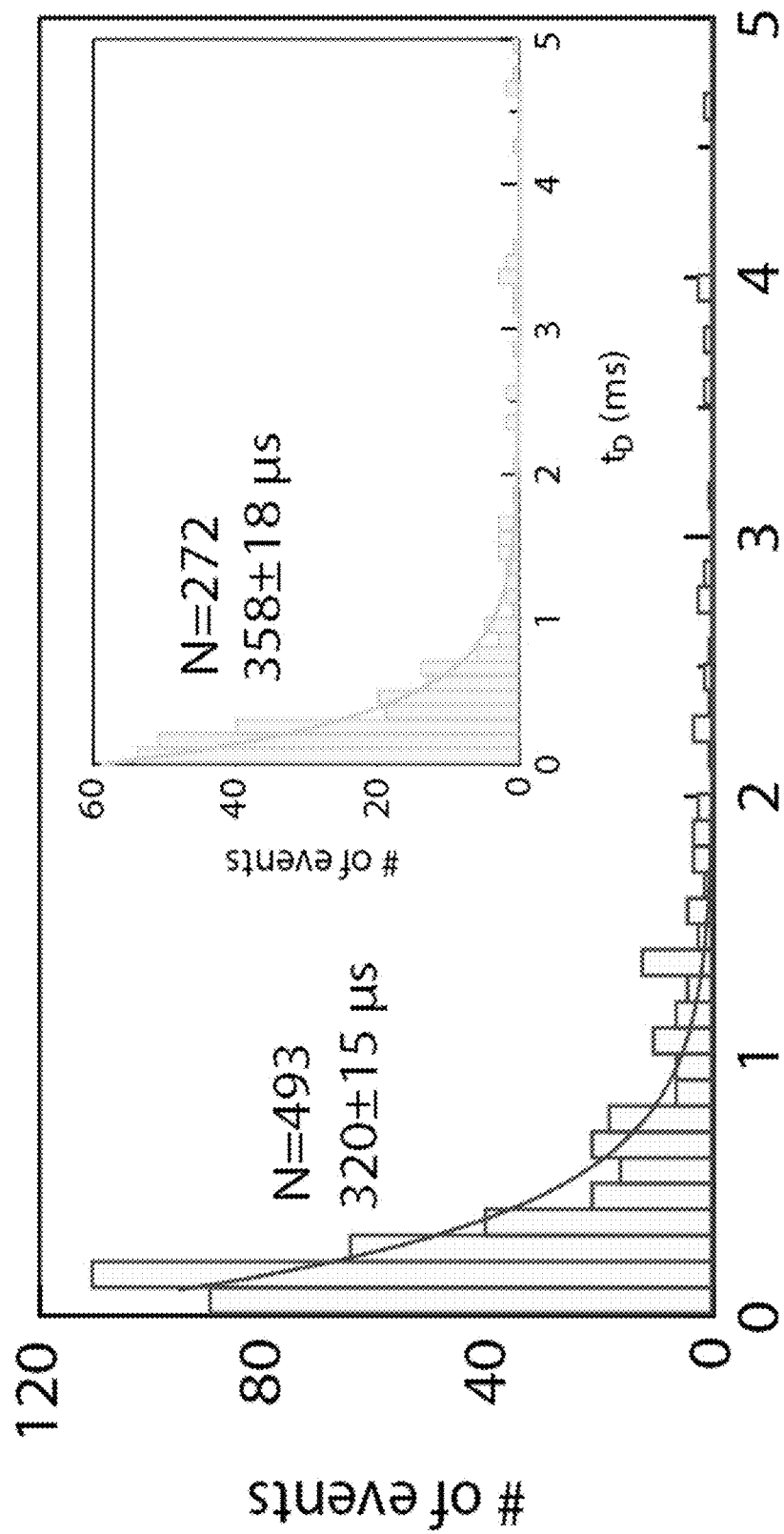

To perform a statistical analysis of all the data, an offline software was developed to identify simultaneous electrical/optical events, as follows: first a smoothed versions of $I_E(t)$ was used to identify the start time, end time and dwell time of each of the electrical blockade events by applying a threshold to the data at three standard deviations away from the open pore level. These time tags were used to extract the corresponding data points in the optical signal $I_O(t)$, along 24 milliseconds of paddings before and after each event. $I_O(t)$ was also subjected to smoothing and thresholding to find the beginning and ending the corresponding optical event (FIG. 4A). In FIG. 4B, the translocation dwell time distributions measured using a STD device (blue markers) and PNW-NP device (gold markers) were compared. The nanopores in these devices were nearly the same size (~4 nm, open pore current 5±0.1 nA). The two measurements yielded nearly the same characteristic dwell times (320±15 µs and 358±18 µs for the STD and PNW-NP, respectively) obtained by tail fit of the distributions by exponential functions. This small difference (about 10%) in the characteristic time can be attributed to slight difference in the nanopore size itself, demonstrating the PNW has little effect on the dwell time of the DNA in the nanopore.

Figure 4C:
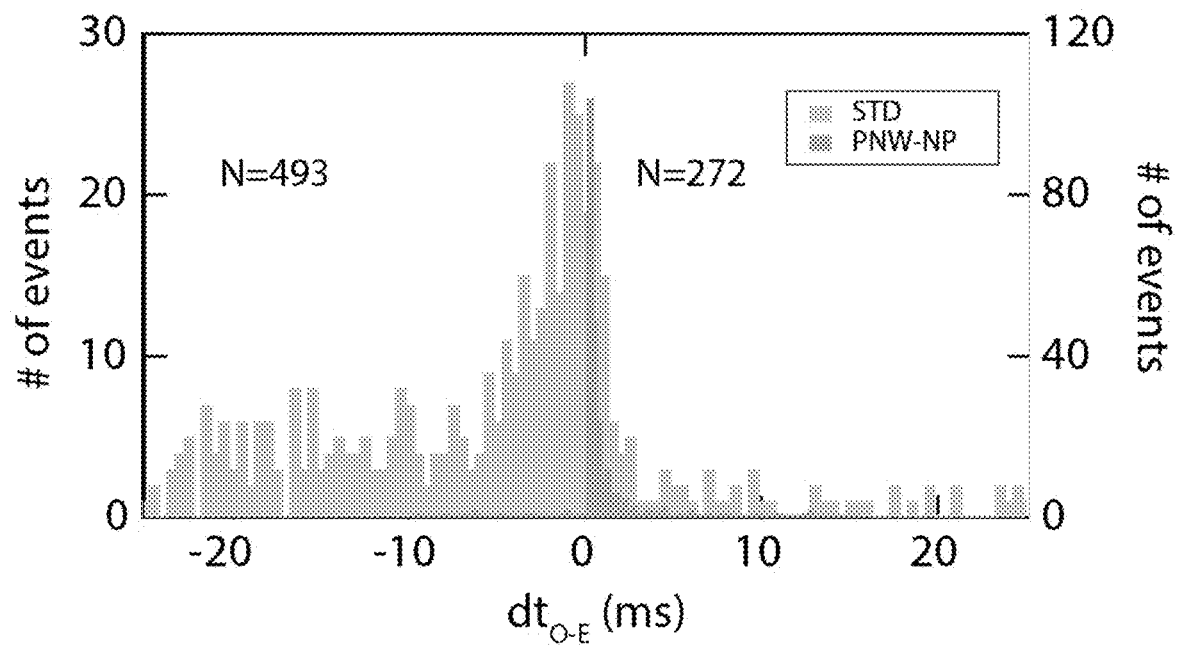

Next the time delay between the rise of the optical signal and the resistive ion current blockade ($\delta t_{O-E}$) was extracted for each and every event in the datasets. Starting from the STD device it was noticed that the optical photon current in the majority of the events (~95%) rises prior to the onset of the electrical blockade event (FIG. 4C, light blue bars), and even more importantly that the distribution of these times is extremely broad. For example, some DNA molecules arrive in the close vicinity of the pore 20 ms before physically entering the pore. This observation is in line with previously published models describing the capture process of DNA onto nanopores: following a rapid drift of the negatively charged DNA towards the pore, one of its ends must be threaded before translocation is commenced. These processes give rise to timescales that can be significantly longer than the translocation time itself. The roughly 5% minority of events in which the algorithm identified the onset of the optical event past the electrical one, can be attributed to mis-identification due to noise in the optical signal measured in the STD device. In contrast, the PNW-NP device (FIG. 4C, gold color) produced a nearly uniform delay time histogram, in which the optical signal in over 95% of the events started synchronously with the electrical signals or at a short delay after the electrical begin time. Specifically, the characteristic variation in $\delta t_{O-E}$ measured in the PNW-NP device is on par with its electrical translocation dwell time distribution (~360 µs). This data shows that Au PNW structure stacked on top of the nanopore ensures that the optical and electrical signals start times are practically synchronized with respect to each other, removing the heterogeneity in the optical start time measured in the STD device. Hence the nanopore acts as a gate, sending individual DNA molecules to the optical sensing zone one at a time, and providing an electrical gating signal. These measurements were reproduced at two different laser intensities (90 µW and 9 uW) giving similar results. Event diagrams showing the blockade current level versus electrical dwell time, as well as the fluorescence intensity versus optical dwell time are shown in FIG. 5F.

Example 5

Thus far it has been shown that the PNW-NP structure provides two essential benefits for single-molecule electro-optical detection in solid-state nanopores, namely: an essentially fluorescence-free background even at high concentrations (FIG. 2B-D) and time synchronization between the electrical and optical signals (FIG. 3E-H).

In order to confirm that the PNW devices boost fluorescence intensity with 640 nm excitation, and to evaluate the optimal PNW diameter, detailed numerical simulations of the device were performed. A model of the PNW-NP structure was constructed in a finite-difference time-domain (FDTD) simulation, as described in the Materials and Methods. The results are summarized in FIGS. 5A-C. The electromagnetic field intensity distribution in the reference STD device was first compared with the PNW-NP device. Both devices were aligned in 3D with respect to the nanopore location, and were excited by identical EM field from the Au side. The ratio of the resulting EM field intensities (PNW-NP over STD) are shown as 2D heat map in FIG. 5A. Maximal enhancement factor of nearly 4-fold is observed at the center of the PNW aperture (x=y=z=0). Notably, in addition to the increase in the field amplitude, the "focusing" of the electromagnetic field onto the PNW opening creates a desirable effect of constricting the excitation to a much smaller zone than the confocal spot (roughly 20 nm versus 200 nm).

Figure 5B:
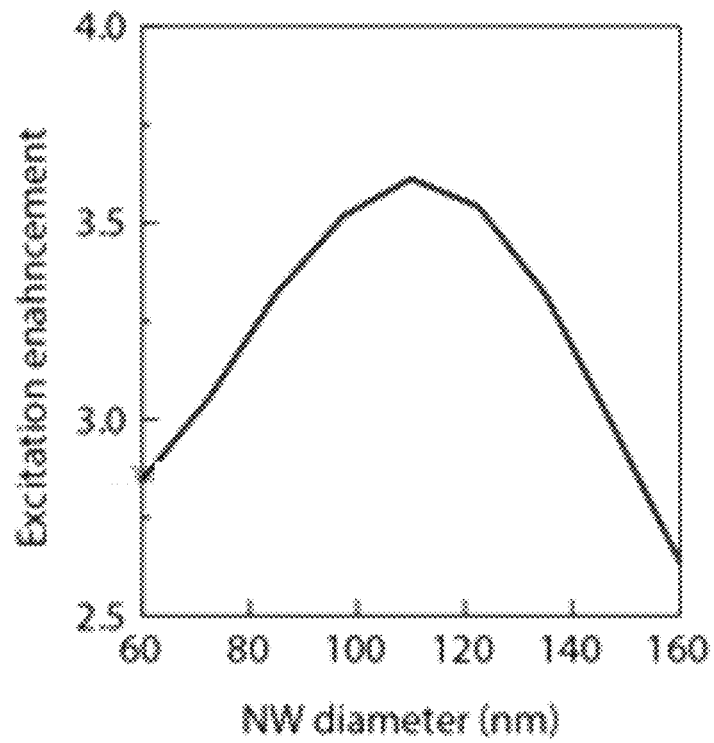
Figure 5C:
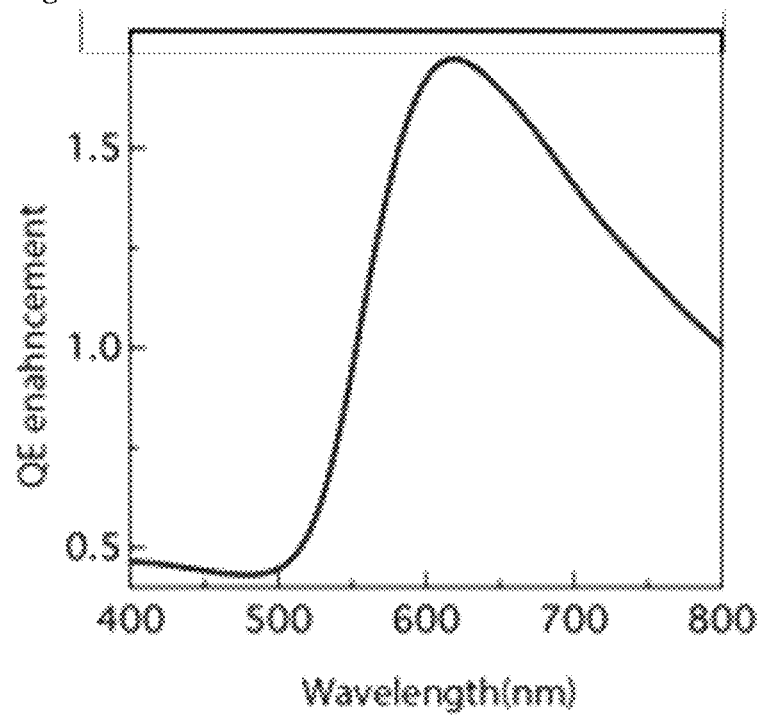

In FIG. 5B, the excitation enhancement at this spot was calculated for varying PNW diameters. The maximum enhancement for the red laser excitation occurs around a 120 nm diameter. Finally, the effect of the PNW on the quantum efficiency (QE) enhancement of the fluorophores was calculated (FIG. 5C). The enhancement in QE compared to pure water was estimated (the intrinsic decay rate was assumed to be unchanged by environment). The results show a relative enhancement at the emission wavelength 660 nm of roughly 1.6. Thus, the expected overall fluorescence enhancement in the system can be estimated as the multiplication of both contributions, namely: $3.6 \times 1.6 = 5.8$.

Based on the FDTD simulations, a 120 nm diameter PNW with a 4 nm NP drilled at its bottom surface was fabricated, and electro-optical translocations experiments using 5 kbp DNA molecules labeled with seven CF640R fluorophores were performed. As a reference a STD device was fabricated, and similar electro-optical measurements were performed keeping the same laser intensity of 9 µW and 300 mV bias. The results are presented in FIG. 5D using the same color codes as before (STD device in blue and PNW-NP in gold). The net photon intensity was evaluated in an event by event basis by first subtracting its background contribution measured prior to the beginning the event. Events which did not show simultaneous electrical and optical rise/drop respectively were disqualified from this analysis. The total net photons emitted during each event were then calculated, as before, and normalized by its corresponding time ($t_O$), to obtain the average fluorescence intensity for each event. In this way biasing of the distributions by a minority of the extremely long dwelling (and hence apparently very bright) events was avoided. The fluorescence intensity histograms presented as solid bars on a semi-log scales were fitted by Gaussian functions having peaks at 43±5 kHz and 468±44 kHz for the STD and PNW-NP devices, respectively. These values reflect photon emission rate of ~6.1 kHz and 69 kHz per fluorophore for the STD and PNW-NP devices, respectively. The fluorescence background level was also measured from each event by averaging roughly 24 milliseconds of the data streams before the beginning of each optical event. The histograms of these values are shown as empty bars in FIG. 5D. Both configurations resulted in similar background level (2.0±0.1 KHz).

Figure 5D:
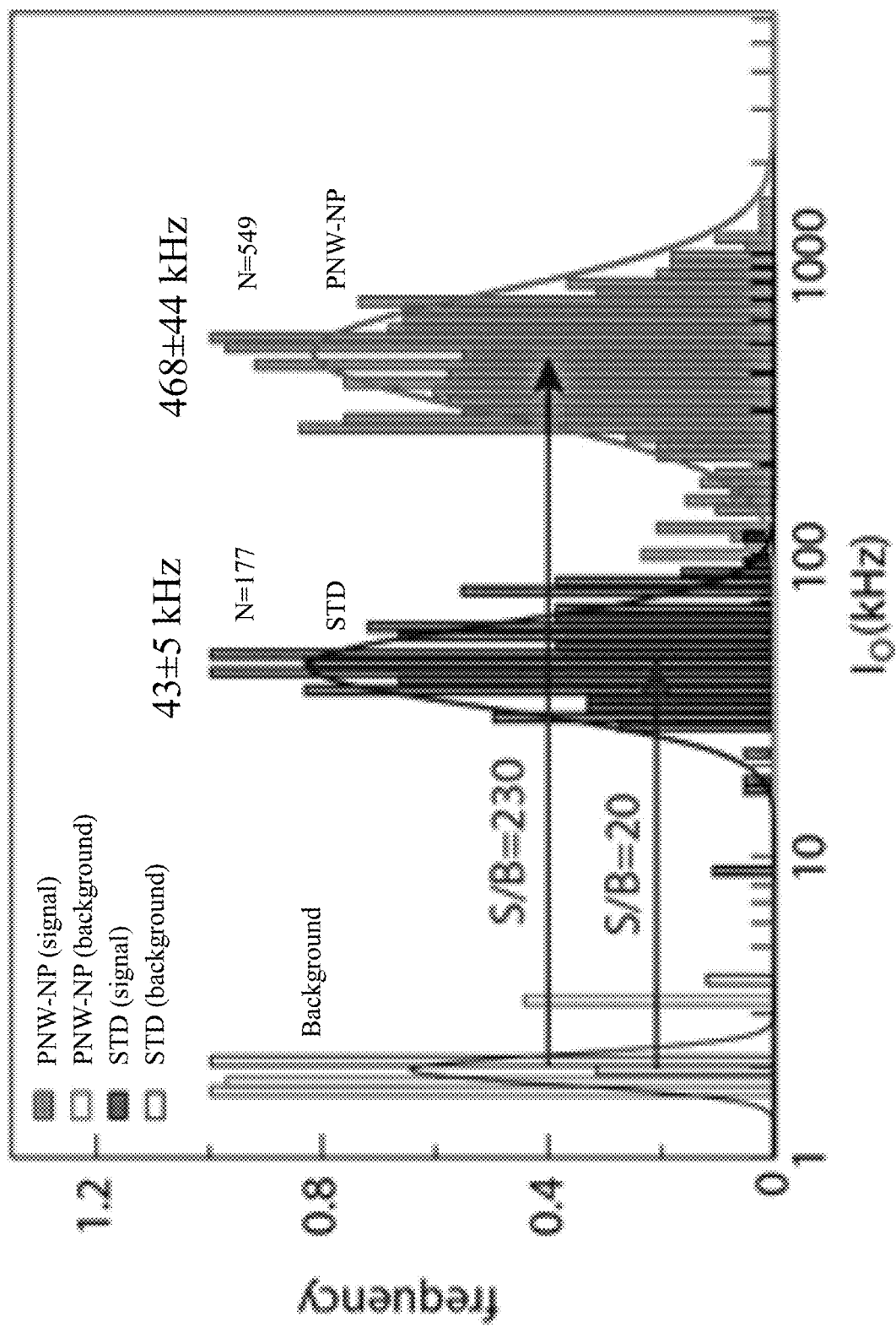
Figure 5E:
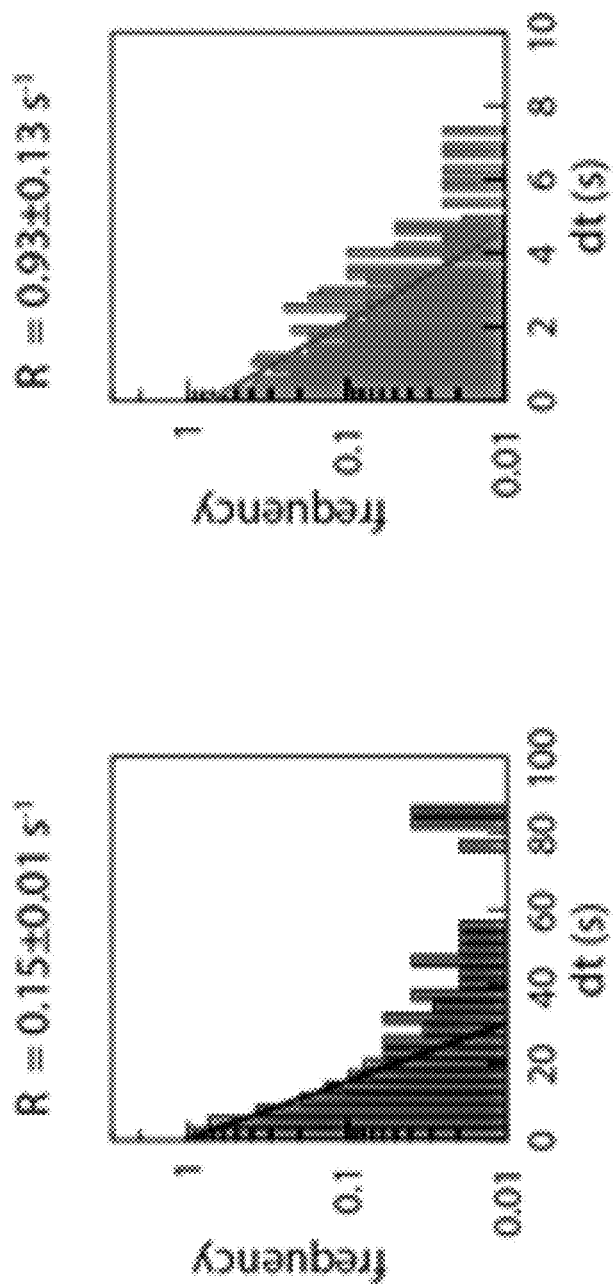
Figure 5F:
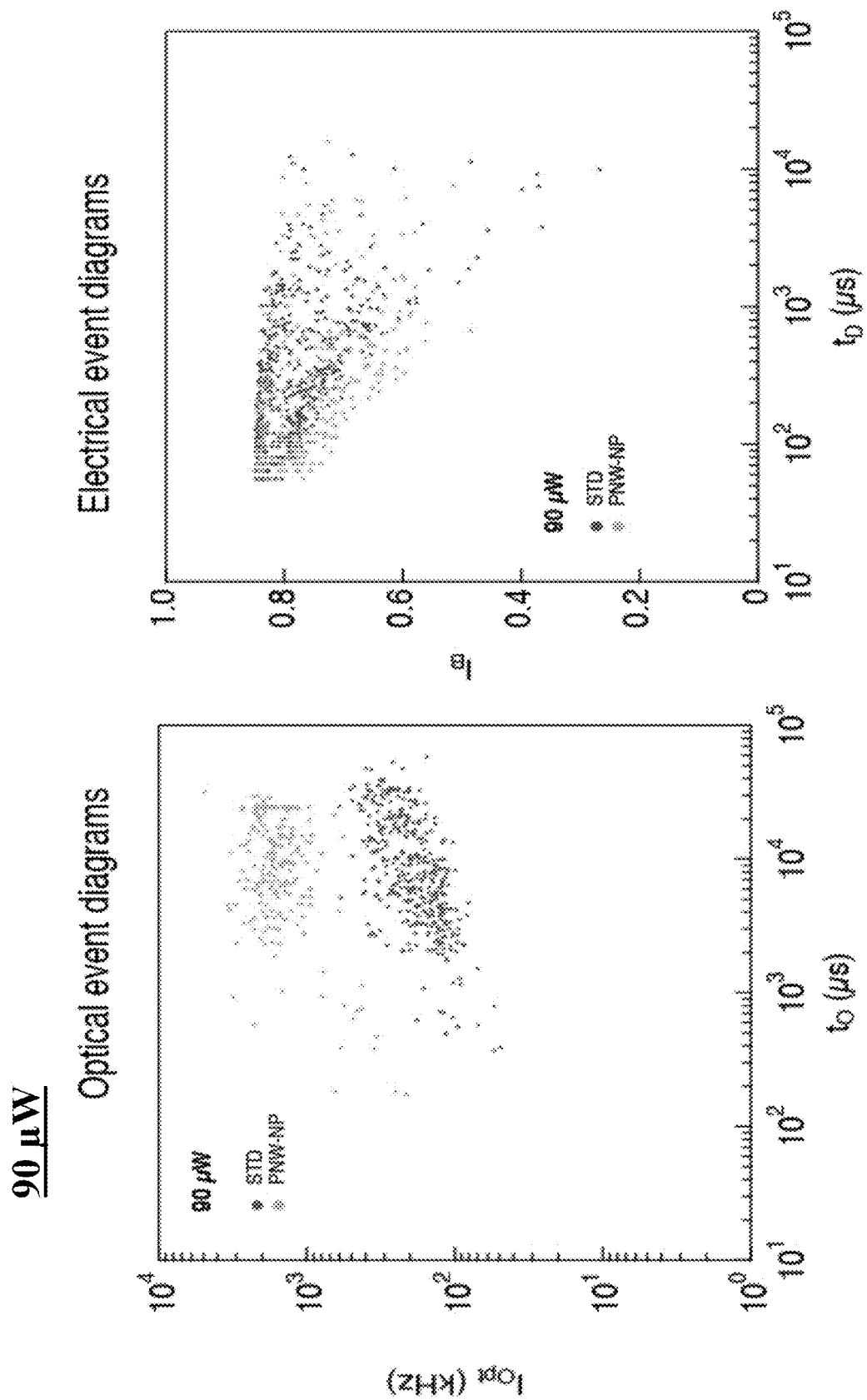
Figure 5F:
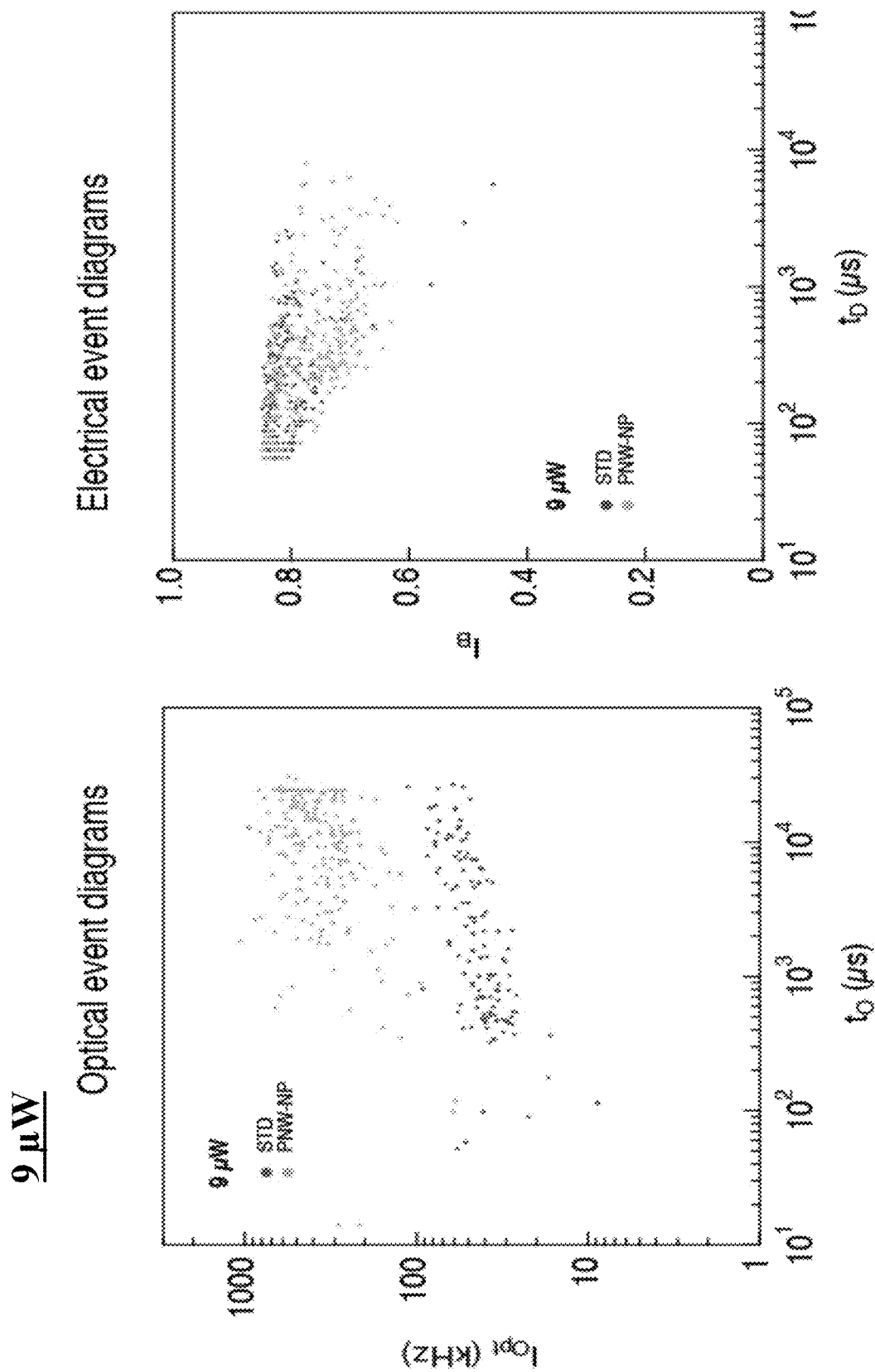

Based on the mean signal and background levels one can evaluate the S/B (signal/background) ratios for the two configurations, as shown in FIG. 5D. S/B of 20 and 230 for the STD and PNW-NP devices were obtained, respectively, reflecting more than 10-fold enhancement in the fluorescence signal. Recalling that these signals result from seven fluorophores it was estimated that the S/B ratios per fluorophore are roughly 3 and 33 for the STD and PNW-NP devices, respectively. It was noted that an S/B of 33 for PNW-NP is significantly better than the quencher-based systems known in the art. As shown in FIG. 5E, the event rate measured using the PNW-NP device is roughly six fold larger than the corresponding one measured in the STD device. Since the experiments were performed using the same voltage (300 mV), DNA molecules and nanopore size (4 nm) this primarily reflects 6-fold larger DNA bulk concentration. Looking back at FIG. 2D, the background level attained using the PNW-NP was practically independent of dye concentration, whereas the STD device was linearly increasing with concentration. FIG. 5D therefore illustrates both gain in net signal and suppression of the fluorescence background in the plasmonic device. These results were further confirmed by repeating the measurements using stronger laser intensity (90 µW) (FIG. 5F).

These results highlight the advantageous aspects that the PNW-NP devices provide towards optical detection of single DNA molecules in nanopores: 1. Fluorescence background is suppressed to effectively a constant level that essentially is independent of bulk dye concentration in the cis chamber. 2. Electrical-optical start times are synchronized, thereby nearly eliminating the stochastic variability associated with the DNA motion near the nanopore. This allows using the electrical ion current pulse as a gate signal to precisely indicate on the rise of the optical signal. 3. A tenfold net enhancement in the observed fluorescence intensity resulting in an extremely bright fluorescence (69 kHz per fluorophore) measured at very low laser excitation (9 µW). These results are supported by numerical simulations of the electromagnetic field intensity in the device and the QE enhancement of the fluorophore, which yield comparable enhancement factors.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:
1. A substrate comprising:
   a. an ion impermeable film comprising at least one ion-conducting nanopore; and
   b. a metallic layer adhered to said film by an adhesion layer, said metallic layer comprising a nanowell structure located adjacent to said nanopore.
2. The substrate of claim 1, wherein said film
   a) is a silicon-based membrane;
   b) has a thickness of less than 50 nanometers (nm); or
   c) both.
3. The substrate of claim 2, wherein said membrane is a silicon nitride (SiNx) membrane.
4. The substrate of claim 1, wherein said nanopore comprises a diameter not greater than 5 nm.
5. The substrate of claim 1, wherein said metallic layer comprises a metal selected from gold, silver, copper and aluminum.

6. The substrate of claim 1, wherein said metallic layer comprises a thickness of between 50 and 150 nm.

7. The substrate of claim 1, wherein said adhesion layer comprises at least one of:
   a. a metal oxide; and
   b. chromium, chromium oxide, titanium or titanium oxide.

8. The substrate of claim 1, wherein said nanowell comprises a diameter between 30 and 150 nm.

9. The substrate of claim 1, wherein said metallic layer and said adhesion layer comprise a thickness sufficient to block at least 50% of light shown thereupon.

10. A system for detecting fluorescence from a molecule, the system comprising:
    a. a substrate of claim 1;
    b. a first and a second liquid reservoir separated by said film;
    c. a means to induce movement of said molecule from said first reservoir to said second reservoir via the nanopore;
    d. a light source capable of exciting said molecule to emit fluorescence, wherein said light source shines into said second reservoir; and
    e. a first detector configured to detect said fluorescence emitted by said molecule.

11. The system of claim 10, wherein the diameter of the nanowell is not greater than half the wavelength of said light emitted by said light source.

12. The system of claim 10, wherein said molecule comprises at least one fluorescent moiety, said molecule is selected from a single-stranded DNA, a double-stranded DNA, an RNA, a cDNA and a polypeptide, or both.

13. The system of claim 10, wherein
    a. said means to induce movement comprises a negative electrode within said first reservoir, and a positive electrode within said second reservoir and said molecule has a negative charge;
    b. a power of said light source is at most 10 microwatts (u W);
    c. said metallic layer is on the second reservoir-side of said membrane;
    d. said detecting comprises sub-millisecond (ms) resolution;
    e. said detector is selected from an active pixel sensor (APS), a charge coupled device (CCD) detector and an Avalanche Photo Diode detector;
    f. said system further comprises a second detector configured to detect ion current flow through said nanopore; or
    g. a combination thereof.

14. The system of claim 13, wherein said system further comprises a second detector configured to detect ion current flow through said nanopore and
    a. said second detector is configured to convert said ion current through said nanopore to a measurable electrical current;
    b. said second detector is a high-gain current amplifier;
    c. said means to induce movement comprises a first electrode within said first reservoir, and a second electrode within said second reservoir, and said high current amplifier is connected to said first and second electrodes;
    d. said first and said second detector are synchronized; or
    e. a combination thereof.

15. A method of detecting fluorescence from a single molecule, the method comprising:
    a. introducing said molecule into said first reservoir of the system of claim 10;
    b. inducing said molecule to move from said first reservoir to said second reservoir via said nanopore;
    c. exciting said molecule within said nanowell to emit fluorescence; and
    d. detecting said fluorescence emitted by said molecule; thereby detecting fluorescence from a single molecule.

16. The method of claim 15, wherein
    a. said detecting comprises sub-millisecond (ms) resolution;
    b. said detecting comprises a high signal to noise ratio;
    c. said metallic layer and said adhesion layer block excitation of fluorochromes in said first reservoir and reduce background fluorescence in said system;
    d. said nanowell enhances fluorescence from said molecule by at least 5-fold;
    e. said system further detects ion current flow through said nanopore and wherein only an event detected simultaneously by fluorescence and electricity is considered detecting fluorescence from said molecule; or
    f. a combination thereof.

17. A method of sequencing a molecule, comprising the method of claim 15 and further comprising assigning an identity to each detected fluorescence, optionally wherein said identity is a nucleic acid base or an amino acid.

18. The substrate of claim 5, wherein said metal is gold.

19. The substrate of claim 1, wherein a side of said nanowell not adhered to said film by said adhesion layer is open.

20. The system of claim 10, wherein said second reservoir is not said nanowell.

* * * * *